(12) United States Patent
Brockway et al.

(10) Patent No.: US 9,072,438 B2
(45) Date of Patent: *Jul. 7, 2015

(54) METHOD AND APPARATUS FOR IDENTIFYING CARDIAC RISK

(71) Applicant: VivaQuant LLC, St. Paul, MN (US)

(72) Inventors: Marina Brockway, St. Paul, MN (US); Brian Brockway, St. Paul, MN (US); Robert Hamlin, Columbus, OH (US)

(73) Assignee: VivaQuant LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/230,439

(22) Filed: Mar. 31, 2014

(65) Prior Publication Data

US 2014/0213921 A1 Jul. 31, 2014

Related U.S. Application Data

(63) Continuation-in-part of application No. PCT/US2011/052371, filed on Sep. 20, 2011, and a continuation-in-part of application No. 12/938,995, filed on Nov. 3, 2010, now Pat. No. 8,632,465, (Continued)

(51) Int. Cl.
| | |
|---|---|
| *A61B 5/04* | (2006.01) |
| *A61B 5/0245* | (2006.01) |
| *A61B 5/0452* | (2006.01) |
| *G06F 17/14* | (2006.01) |
| *G06K 9/00* | (2006.01) |
| *A61B 5/0408* | (2006.01) |
| *A61B 7/00* | (2006.01) |
| *A61B 5/00* | (2006.01) |
| *G06F 19/00* | (2011.01) |

(52) U.S. Cl.
CPC ........... *A61B 5/0245* (2013.01); *A61B 5/04017* (2013.01); *A61B 5/0452* (2013.01); *G06F 17/14* (2013.01); *G06K 9/0051* (2013.01); *G06K 9/0053* (2013.01); *A61B 5/7253* (2013.01); *A61B 5/0006* (2013.01); *A61B 5/04087* (2013.01); *A61B 7/00* (2013.01); *G06F 19/3431* (2013.01)

(58) Field of Classification Search
None
See application file for complete search history.

(56) References Cited

U.S. PATENT DOCUMENTS

| | | | |
|---|---|---|---|
| 5,090,418 A | 2/1992 | Squires et al. | |
| 5,279,283 A * | 1/1994 | Dillon | 601/24 |

(Continued)

FOREIGN PATENT DOCUMENTS

WO   2013/043157 A2   3/2013

OTHER PUBLICATIONS

B. Widrow, et al., "Adaptive noise cancelling: principles and applications," IEEE Proc., vol. 63, No. 12, pp. 1692-1716, Dec. 1975.

(Continued)

*Primary Examiner* — Brian T Gedeon
(74) *Attorney, Agent, or Firm* — Crawford Maunu PLLC

(57) ABSTRACT

A cardiac-based metric is computed based upon characteristics of a subject's cardiac function. In accordance with one or more embodiments, the end of a mechanical systole is identified for each of a plurality of cardiac cycles of a subject, based upon an acoustical vibration associated with closure of an aortic valve during the cardiac cycle. The end of an electrical systole of an electrocardiogram (ECG) signal for each cardiac cycle is also identified. A cardiac-based metric is computed, based upon a time difference between the end of the electrical systole and the end of the mechanical systole, for the respective cardiac cycles.

20 Claims, 15 Drawing Sheets

Related U.S. Application Data application No. 14/230,439, which is a continuation-in-part of application No. 13/172,415, filed on Jun. 29, 2011, now Pat. No. 8,433,395, and a continuation-in-part of application No. 12/938,995, filed on Nov. 3, 2010, now Pat. No. 8,632,465, application No. 14/230,439, which is a continuation of application No. 13/668,898, filed on Nov. 5, 2012, now Pat. No. 8,688,202.

(60) Provisional application No. 61/257,718, filed on Nov. 3, 2009, provisional application No. 61/366,052, filed on Jul. 20, 2010, provisional application No. 61/359,462, filed on Jun. 29, 2010, provisional application No. 61/370,026, filed on Aug. 2, 2010, provisional application No. 61/555,165, filed on Nov. 3, 2011.

(56) References Cited

U.S. PATENT DOCUMENTS

| | | | |
|---|---|---|---|
| 5,521,851 | A | 5/1996 | Wei et al. |
| 5,792,065 | A | 8/1998 | Xue et al. |
| 5,817,027 | A | 10/1998 | Arand et al. |
| 5,827,195 | A | 10/1998 | Lander |
| 5,987,352 | A | 11/1999 | Klein et al. |
| 6,389,308 | B1 | 5/2002 | Shusterman |
| 6,589,189 | B2 | 7/2003 | Meyerson et al. |
| 6,690,959 | B2 | 2/2004 | Thompson |
| 6,701,170 | B2 | 3/2004 | Stetson |
| 6,822,564 | B2 | 11/2004 | Al-Ali |
| 7,096,060 | B2 | 8/2006 | Arand et al. |
| 7,115,096 | B2 | 10/2006 | Siejko et al. |
| 7,236,819 | B2 | 6/2007 | Brockway et al. |
| 7,272,265 | B2 | 9/2007 | Kouri et al. |
| 7,376,453 | B1 | 5/2008 | Diab et al. |
| 7,627,369 | B2 | 12/2009 | Hunt |
| 7,672,717 | B1 | 3/2010 | Zikov et al. |
| 7,840,259 | B2 | 11/2010 | Xue et al. |
| 7,846,104 | B2 * | 12/2010 | MacQuarrie et al. ......... 600/481 |
| 8,086,304 | B2 | 12/2011 | Brockway et al. |
| 8,201,330 | B1 | 6/2012 | Rood et al. |
| 8,214,007 | B2 | 7/2012 | Baker et al. |
| 8,271,073 | B2 | 9/2012 | Zhang et al. |
| 8,348,852 | B2 | 1/2013 | Bauer et al. |
| 8,460,189 | B2 | 6/2013 | Libbus et al. |
| 8,478,389 | B1 | 7/2013 | Brockway et al. |
| 2005/0010120 | A1 | 1/2005 | Jung et al. |
| 2005/0234361 | A1 | 10/2005 | Holland |
| 2005/0283090 | A1 | 12/2005 | Wells |
| 2007/0219453 | A1 | 9/2007 | Kremliovsky et al. |
| 2007/0219455 | A1 | 9/2007 | Wong et al. |
| 2007/0260151 | A1 | 11/2007 | Clifford |
| 2007/0265508 | A1 | 11/2007 | Sheikhzadeh-Nadjar |
| 2008/0065158 | A1 | 3/2008 | Ben-Ezra et al. |
| 2008/0097537 | A1 | 4/2008 | Duann et al. |
| 2008/0183093 | A1 | 7/2008 | Duann et al. |
| 2008/0200832 | A1 | 8/2008 | Stone |
| 2008/0228094 | A1 * | 9/2008 | Audet et al. ............ 600/513 |
| 2008/0255464 | A1 * | 10/2008 | Vincent ................ 600/514 |
| 2009/0069703 | A1 | 3/2009 | Takla et al. |
| 2009/0222262 | A1 | 9/2009 | Kim et al. |
| 2010/0234916 | A1 * | 9/2010 | Turcott et al. ............ 607/30 |
| 2012/0165691 | A1 | 6/2012 | Ting et al. |
| 2012/0197144 | A1 | 8/2012 | Christ et al. |
| 2012/0232417 | A1 | 9/2012 | Zhang |
| 2013/0109937 | A1 | 5/2013 | Banet et al. |
| 2014/0005988 | A1 | 2/2014 | Brockway |

OTHER PUBLICATIONS

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).

G. Moody, W. Muldrow, and R. Mark, "A noise stress test for arrhythmia detectors," Computers in Cardiology, pp. 381-384 (1984).

K. R. Rao and P. Yip, "Discrete Cosine Transform: Algorithms, Advantages, Applications," San Diego, CA: Academic (1990).

J. Woods. Subband Coding, Kluwer Academic Press (1990).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993.

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455.

Y. Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution,"Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).

J._Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A. Hyvërinen "New Approximations of Differential Entropy for Independent Component nalysis and Projection Pursuit," In Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

American National Standard ANSI/AAMI EC57:1998, Testing and Reporting Performance Results of Cardiac Rhythm and ST Segment Measurement Algorithms.

Testing and reporting performance results of cardiac rhythm and ST-segment measurement algorithms ANSI/AAMI EC57:1998.

L. Torres- Pereira, et. al. "A Biotelemetric Heart Sound Monitoring System," in Proceedings of the 14th International Symposium on Biotelemetry. Marburg, 1998.

A. Hyvärinen, "Fast and Robust Fixed-Point Algorithms for Independent Component Analysis," IEEE Transactions on Neural Networks, vol. 10, No. 3, pp. 626-634 (May 1999).

J.-F. Cardoso, "High-Order Contrasts for Independent Component Analysis," Neural Comput., vol. 11, No. 1, pp. 157-192 (1999).

(56) References Cited

OTHER PUBLICATIONS

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

S. Mallat, "A Wavelet Tour of Signal Processing," Academic Press, 1999.

Langley, P.; Di Bernardo, D.; Murray, A.; Comparison of three measures of QT dispersion. Computers in Cardiology 1999 pp. 69-72.

Goldberger Al et al. PhysioBank, PhysioToolkit, and PhysioNet: components of a new research resource for complex physiologic signals. Circulation 101(23): e215-e220, 2000 (Jun. 13).

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression Conference, pp. 523-541 (2000).

L. K. Saul and J. B. Allen, "Periodic component analysis: An eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.

C. Taswell, "The What, How, and Why of Wavelet Shrinkage Denoising," Computing in Science and Engineering, vol. 2, No. 3, pp. 12-19 (2000).

J. S. Richman and J. R. Moorman, Physiological time-series analysis using approximate entropy and sample entropy Am. J. Physiol. 278, H2039 (2000).

K. Sayood, "Introduction to Data Compression," Academic Press 2000.

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

R. Mayerburg. Sudden cardiac death: exploring the limits of our knowledge. Journal of Cardiovascular Electrophysiology, vol. 12, No. 3, Mar. (2001).

M. Brennan, M. Palaniswami, and P. Kamen. Do Existing Measures of Poincaré Plot Geometry Reflect Nonlinear Features of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in a Signal Dictionary," Neural Computation. vol. 13, pp. 863-882 (2001).

Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1.

M. Costa, A. L. Goldberger, and C.-K. Peng, Multiscale Entropy Analysis of Complex Physiologic Time Series, Phys. Rev. Lett. 89, 6, (2002).

B. U. Kohler, C. Hennig, R. Orglmeister. The principles of software QRS detection. IEEE Engineering in Medicine and Biology Magazine, vol. 21, No. 1. (2002), pp. 42-57.

Kellermann, et al.,"A mobile phone based alarm system for supervising vital parameters in free moving rats," BMC Research Notes 2012, 5:119, Feb. 23, 2012.

http://www.simplehelp.net/2006/09/12/how-to-set-up-outlook-2003-for-email/.

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Madalena Costa.et. al. Multiscale entropy analysis of biological signals. Physical Review E 71, 021906 s2005d, 2005.

M. Alghonierny and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

Inan, O.T.; Giovangrandi, L.; Kovacs, G.T.A.; Robust Neural-Network-Based Classification of Premature Ventricular Contractions Using Wavelet Transform and Timing Interval Features , IEEE Transactions on Biomedical Engineering vol. 53 , Issue: 12 , , pp. 2507-2515, 2006.

L. Smith, A tutorial on Principal Components Analysis, Feb. 26, 2002.

(56) References Cited

OTHER PUBLICATIONS

Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.

K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).

K. Todros and J. Tabrikian, "Blind Separation of Independent Sources Using Gaussian Mixture Model," IEEE Transactions on Signal Processing, vol. 55, No. 7, pp. 3645- 3658 (Jul. 2007).

R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).

X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).

R Schimpf, Ch Antzelevitch, D Haghi, C Giustetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008 ; 5(2): 241-245.

Sarkar S, Ritscher D, Mehra R. A detector for a chronic implantable atrial tachyarrhythmia monitor. IEEE Trans Biomed Eng. Mar. 2008;55(3):1219-24.

M. Malik, K. Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and fullband electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14 , Issue: 2, pp. 152-159, 1995.

Dash S, Chon KH, Lu S, Raeder EA. Automatic real time detection of atrial fibrillation. Ann Biomed Eng. Sep. 2009;37(9):1701-9. Epub Jun. 17, 2009.

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Piccini, et al, Predictors of sudden cardiac death change with time after myocardial infarction: results from the VALIANT trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S.Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) "Honey Carbon: A Review of Graphene" Chem. Rev. 110:132-145.

Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Thwart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg, National Institute of Health, PhysioBank Archive, Dec. 11, 2014.

http://www.physionet.org/physiobank/database/mitdb/, National Institute of Health, PhysioBank Archive, Dec. 11, 2014, Tsalaile, et al. "Blind Source Extraction of Heart Sound Signals From Lung Sound Recordings Exploiting Periodicity of the Heart Sound," ICASSP 2008 IEEE, p. 461-464.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

\* cited by examiner

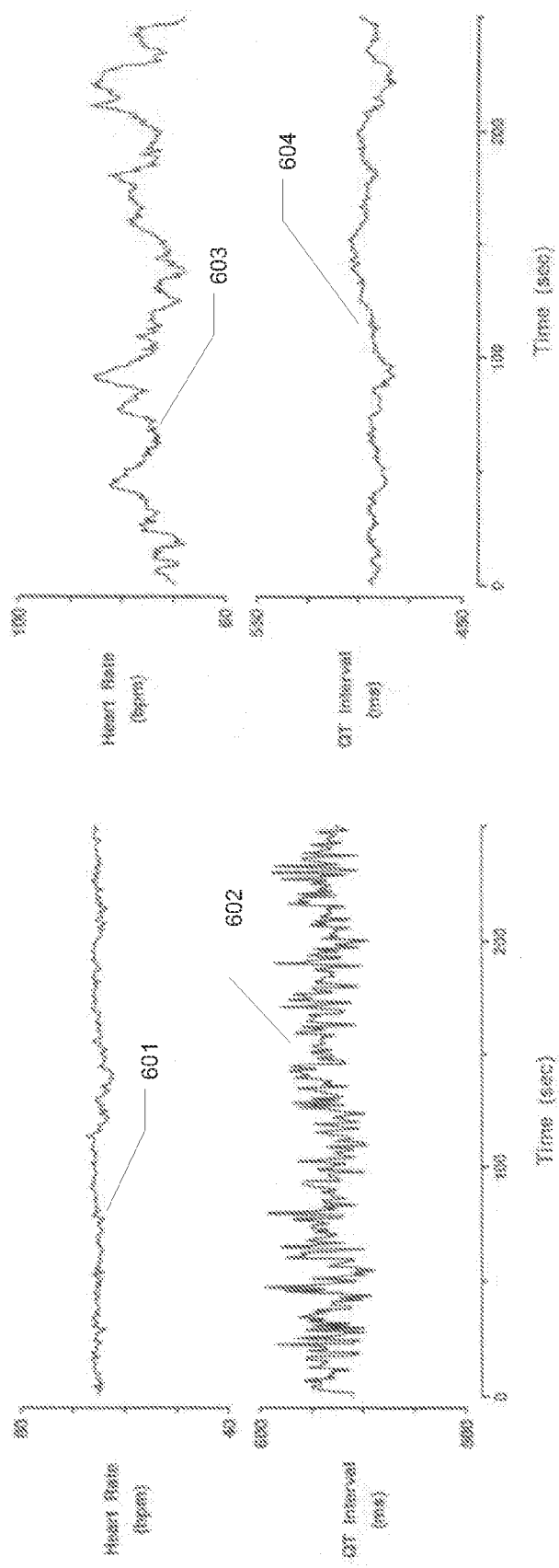

METHOD AND APPARATUS FOR IDENTIFYING CARDIAC RISK

FIELD

The present disclosure is related to characterizing cardiac-based function.

BACKGROUND

Understanding the risk of arrhythmias, such as those that may stem from pharmaceuticals and cardiac pathologies, can be important in order to apply desirable and cost-effective therapeutic approaches and treat diseases based upon patient-specific medical conditions and risks for developing a dangerous arrhythmia. For instance, understanding such risk can be helpful for patients diagnosed with cardiac diseases including heart failure and myocardial ischemia. The risk of arrhythmias is often assessed in both preclinical and clinical studies. For instance, the proarrhythmic risk of medications is often assessed in preclinical studies using several approaches. Clinical studies involving the QT interval of a cardiac cycle, such as those involving measurement of QT prolongation on healthy human subjects, can also be performed to assess the proarrhythmic risk of new medications.

However, such studies and assessments have been challenging to implement. It is often desirable to perform these assessments on ambulating human and animal subjects. However, performing these assessments on ambulatory subjects is difficult or impractical because either the required measurements are highly invasive or because the signals acquired using minimally invasive or non-invasive sensing techniques often result in signals that are sufficiently noisy and for which consistently accurate measurements are not possible. As evidence of these challenges, a significant percentage of pharmaceuticals that show no indication of proarrhythmic risk in preclinical studies eventually demonstrate evidence of proarrhythmic risk later in either development or post marketing. In addition, commonly used risk indicators are heart rate dependent and can hence be difficult to interpret. One of the unfortunate consequences of the lack of a reliable and sensitive cardiac risk metric is that preclinical studies sometimes falsely eliminate safe and effective drugs from the development pipeline based on metrics that have low predictive accuracy.

Techniques used to assess proarrhythmic risk in clinical care have also been challenging to implement in accurately assessing the risk of cardiac arrhythmias, such as for patients that have experienced myocardial infarction and those diagnosed with systolic heart failure and coronary artery disease. Unfortunately, the vast majority of deaths caused by dangerous arrhythmias occur in populations where existing techniques have proven ineffective and no practical and cost-effective options exist to accurately assess arrhythmic risk in these populations. Further, analyzing characteristics on ambulatory patients can be difficult. These and other characteristics have been challenging to the characterization of cardiac function, and risk associated therewith.

SUMMARY

Various aspects of the present disclosure are directed to devices, methods and systems for assessing the risk of cardiac arrhythmias, in a manner that addresses challenges and limitations including those discussed above.

In accordance with one or more embodiments, a cardiac-based metric is computed for a subject as follows. The end of a mechanical systole is identified, for each of a plurality of cardiac cycles of the subject, based upon an acoustical vibration associated with closure of an aortic valve during the cardiac cycle. The end of an electrical systole of an electrocardiogram (ECG) signal is also identified for the cardiac cycle. A time difference between the end of the electrical systole and the end of the mechanical systole for each of the plurality of cardiac cycles (e.g., collectively) is used to compute the cardiac-based metric. Using this approach, mechanical characteristics of the valve closing can be used together with electrical characteristics of the ECG, to provide an indication of cardiac function that measures electro-mechanical dysynchrony. In connection with this and other embodiments, it has been discovered that, by using this combined mechanical and electrical detection approach, challenges such as those above, as may be applied to measuring EMW, processing beat-to-beat information, and otherwise characterizing cardiac risk can be addressed. Further, the embodiments described here provide an approach that facilitates these cardiac electromechanical characteristics to be accurately measured on ambulating subjects.

In accordance with various example embodiments, mechanical and electrical dysynchrony is measured as the time difference (e.g., electro-mechanical window—EMW) between a point in a cardiac cycle that corresponds to the end of mechanical systole (MS) and a point that corresponds to the end of electrical systole (ES). EMW=end of MS (MSend)−end of ES (ESend). In one embodiment, end of MS is identified by detecting the S2 heart sound. In one embodiment, end of ES is identified by detecting the end of the T-wave (i.e. T-wave offset). In one embodiment, short term and long term instability of the EMW or QT interval is computed to enhance the predictive value. In one embodiment, complexity of beat-to-beat dynamics of EMW or QT interval is quantified by computing multiscale entropy parameters and evaluating the trend of these parameters over multiple scales. In one embodiment EMW is combined with one or more of a) QRS duration, b) QT interval, c) short term QT variability and d) T-wave alternans to improve predictive value. In various embodiments, the S2 heart sound is sensed using a microphone or accelerometer and its occurrence is detected from the sensed signal using techniques such as those involving multi-domain signal processing (MDSP) techniques as discussed herein. For instance, the microphone or accelerometer can be integrated into an adhesive-backed ECG sensing electrode. In various embodiments T-wave offset is detected by denoising and processing an ECG, or by using MDSP techniques as discussed herein.

BRIEF DESCRIPTION OF THE DRAWINGS

The disclosure may be more completely understood in consideration of the following detailed description of various embodiments in connection with the accompanying drawings, in which:

FIG. 4A shows an example of relationships between HR and QT dynamics in a diseased heart, consistent with one or more example embodiments;

FIG. 4B shows an example of relationships between HR and QT dynamics in a normal heart, consistent with one or more example embodiments;

DETAILED DESCRIPTION

Figure 1A:
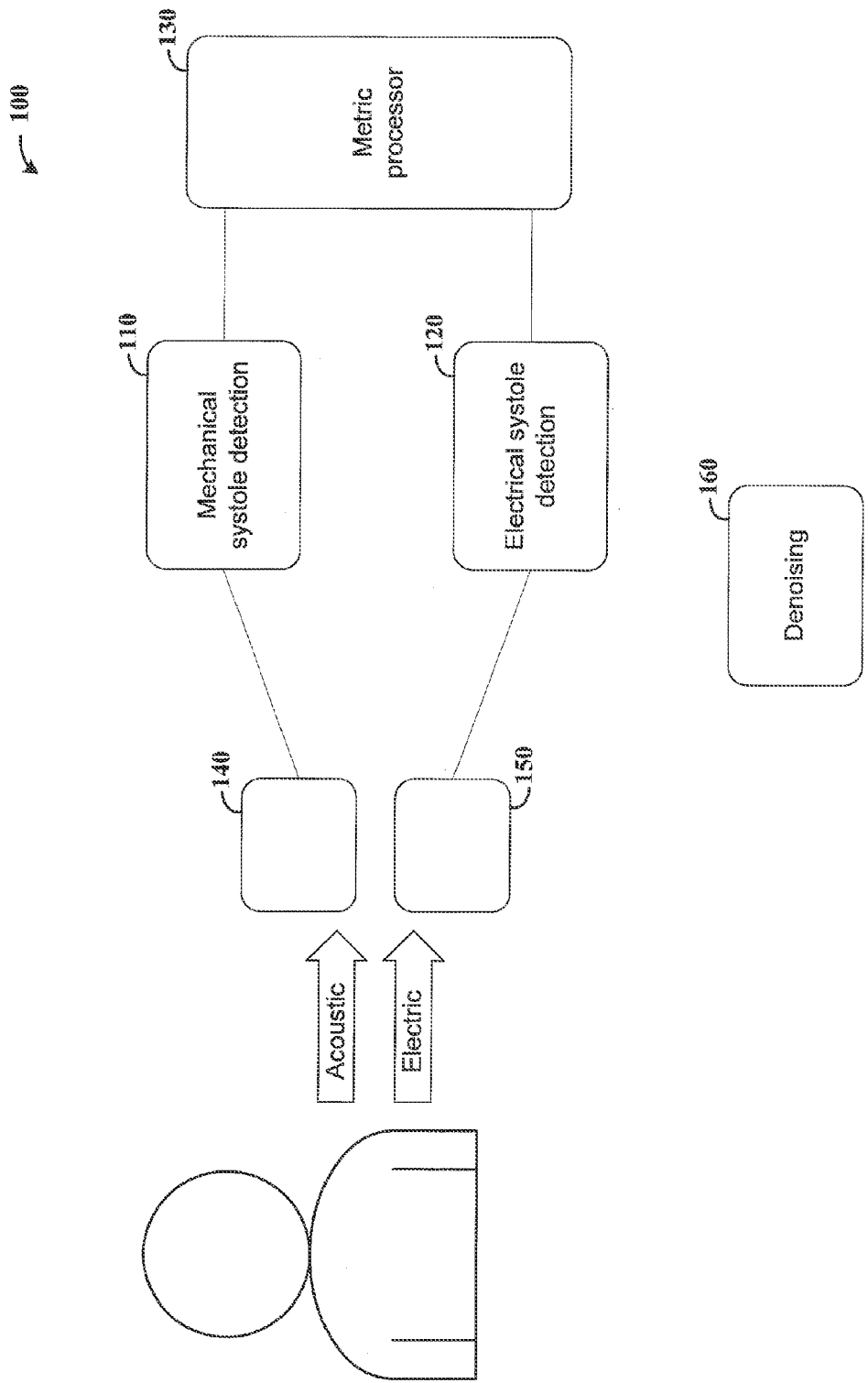
FIG. 1A shows an apparatus for characterizing a cardiac-based metric, in accordance with an example embodiment.

Aspects of the present disclosure relate to methods and apparatuses involving measuring and detecting characteristics of cardiac function, such as alterations in cardiac function that precede the occurrence of arrhythmia or are indicative of an increased risk of arrhythmia. Certain aspects relate to methods and systems for measuring an electro-mechanical window (EMW) using heart sounds and evaluating beat-to-beat values of the EMW and other information such as QT interval to indicate arrhythmic risk. In some implementations, EMW is used to address a number of challenges to implementing risk indicators, as discussed above, by operating generally independent of heart rate.

In accordance with another example embodiment, a cardiac-based metric is computed using both mechanical and electrical systole for each of a plurality of cardiac cycles as follows. The end of a mechanical systole is detected using an acoustical vibration associated with closure of an aortic valve (e.g., the S2 heart sound) that occurs during the cardiac cycle. The end of an electrical systole is also detected using electrocardiogram (ECG) signal for the cardiac cycle. The cardiac-based metric is computed using respective time differences between the end of the mechanical and electrical systoles for each of the plurality of cardiac cycles (e.g., by computing the time difference between the end of the electrical systole and the end of the mechanical systole for each cardiac cycle). These respective ends of the mechanical and electrical systole may, for example, be identified by processing signal data such as acoustical heart sound data and ECG data shown in and described in connection with figures below (e.g., identifying an S2 sound and a T-wave offset), within a computer-type circuit as described herein and using characteristics of the respective signals. Such a computer-type circuit can also be implemented to compute the cardiac-based metric using time differences collected from multiple cardiac cycles, and therein provide an indication of the collective differences as applicable to, for example, proarrhythmic risk.

The respective ends of the mechanical and electrical systoles are identified using one or more of a variety of approaches, in accordance with various example embodiments. For instance, the end of the mechanical systole can be identified using an acoustical signal containing energy associated with both the closure of the aortic valve and noise energy. In an embodiment, the acoustical signal is decomposed from a first domain into subcomponents of the acoustical signal in a second domain, and at least two of the subcomponents are identified as exhibiting an energy level of which at least half is associated with closure of the aortic valve. The identified subcomponents are mathematically combined to compute a time function that identifiably changes in value upon aortic valve closure.

In one embodiment, the end of the electrical systole can be identified using an ECG signal including a noise component and an ECG component originating from heart tissue of the subject. The ECG signal is decomposed from a first domain into subcomponents of the ECG signal in a second domain, and the location of a QRS complex of the cardiac cycle is identified using a spatial distribution of the subcomponents. A first time window in the cardiac cycle that includes the QRS complex is identified, as is at least one additional time window in the cardiac cycle that does not include the QRS complex. For each time window, subcomponents having more energy corresponding to the ECG component than noise energy are identified (e.g., those subcomponents within the respective window in which at least 50% of the energy thereof pertains to the actual ECG signal from the subject's heart, relative to noise). A denoised ECG is then constructed in the first domain by combining the identified subcomponents. The denoised ECG can then be analyzed using ECG analysis algorithms to identify the end of the electrical systole.

In another embodiment, the end of the electrical systole is identified by similarly decomposing an ECG signal from a first domain into subcomponents of the ECG signal in a second domain, and then identifying the location of the QRS complex of the cardiac cycle based upon a spatial distribution of the subcomponents. A T-wave offset search window is established, relative to the location of the QRS complex, and at least two subcomponents are identified as having an energy value that is predominantly energy of a T-wave of the cardiac cycle. The at least two identified subcomponents are mathematically combined to compute an emphasis signal having an identifiable inflection corresponding to a location of the T-wave offset. The T-wave offset location is identified based upon a characteristic of the emphasis signal, and is used to identify the end of the electrical systole.

The cardiac-based metric is computed using one or more of a variety of approaches. In some embodiments, the metric is computed by computing one of a mean, a median, variance, standard deviation, and standard error of the time difference for each cardiac cycle. In certain embodiments, the cardiac-based metric is computed by computing a short-term instability metric based on one of the mean, standard deviation and root mean square of successive differences between beat-to-beat values in a window segment including the plurality of cardiac cycles, in which the beat-to-beat values corresponding to heartbeats that define the successive start of the cardiac cycles. In another embodiment, a long-term instability metric is computed as a variance in the beat-to-beat values, multiplied by two and then subtracting the computed short term instability metric therefrom.

In connection with the above and other embodiments, it has been discovered that the measurement of synchrony between mechanical and electrical systole can be particularly useful in addressing issues as discussed above, and further that such approaches can be implemented together to obtain desirable characterizations of cardiac function under conditions in which noise has been challenging to address (e.g., with ambulatory subjects). It has further been discovered that these approaches can be achieved without necessarily involving invasive-type approaches, complex procedures such as the use of echocardiography to measure the velocity of heart tissue, and mitigates/avoids errors relating to changes in heart rate. Acoustical vibrations that occur as a result of aortic valve closure (e.g., S2 sounds) can be used in this context to measure EMW to achieve results similar to approaches involving left ventricular pressure (LVP) that are described in the literature. EMW, which is independent of heart rate, can be used to obtain a sensitive cardiac-based metric (e.g., by detecting changes in EMW that indicate an increased risk of arrhythmia on the order of 200%, relative to changes in QT and corrected $QT(QT_c)$ indicative of increased arrhythmic risk on the order of 30%).

Various embodiments are directed to non-invasive and minimally invasive measurements of EMW in ambulatory patients, such as for providing an assessment of arrhythmic risk. In some implementations, risk indicators are obtained on ambulatory subjects over a period of time (e.g., 24 hours). These approaches can be implemented, for example, to address alterations that can impact cardiac function and arrhythmic risk indicative of the changes that occur at the cellular level, which vary with time, stress, and other stimuli. Further, these risk indicators can be obtained from ambulatory patients while addressing noise from the patients' surroundings as well as noise that occurs due to respiration and patient movement (e.g., clothing rubbing). In some embodiments, such approaches are implemented using S2 heart sounds, an approach that allows for minimally invasive or non-invasive detection of MSend in ambulatory subjects. Such approaches are further facilitated by the use of MDSP signal processing techniques to accurately detect MSend and ESend when the signals are corrupted with noise.

Many embodiments described herein refer to signal processing approaches such as "multi-domain signal processing" (MDSP), which refers to one or more of various embodiments described in U.S. patent application Ser. Nos. 12/938,995, 13/092,530, and 13/172,415, which may be implemented in accordance with one or more embodiments herein. These patent documents, as well as the patent documents therein to which benefit is claimed and the references cited therein, are fully incorporated herein by reference. In some embodiments, such an MDSP-based approach is used to process physiological information captured from ambulatory subjects in order to measure and detect alterations in cardiac function that are indicative of arrhythmic risk. In the following discussion, reference is made to cited references listed in a numbered order near the end of this document, which are fully incorporated herein by reference. These references may assist in providing general information regarding a variety of fields that may relate to one or more embodiments of the present disclosure, and further may provide specific information regarding the application of one or more such embodiments.

Turning now to the figures, FIG. 1A shows an apparatus 100 for characterizing a cardiac-based metric of a subject (i.e., a patient), in accordance with another example embodiment. The apparatus 100 includes a mechanical systole module 110, an electrical systole module 120, and a processing module 130. The mechanical systole module 110 operates to process acoustical data received from an acoustical signal acquisition module 140, in which the acoustical data includes heart sound data of the subject, and to provide an indication of an end of the mechanical systole for the subject. In some implementations, the acoustical signal acquisition module includes a microphone or other audio detection-type devices. The electrical systole module 120 operates to process electrical cardiac data, such as ECG data, for the subject and received via an electrical signal acquisition module 150, and to provide an indication of an end of the electrical systole for the subject. For instance, the electrical signal acquisition module 150 may include ECG leads that are coupled to acquire an ECG signal from the subject. In some instances, the mechanical and electrical signal acquisition modules 140 and 150 are combined for application to the subject, such as via an adhesive component including both electrical and acoustical pickup circuits.

The processing module 130 is coupled to receive data from both the mechanical systole module 110 and the electrical systole module 120, respectively indicative of the end of the mechanical systole and the electrical systole for the subject. The processing module 130 uses this data to compute a cardiac-based metric, such as may be related to proarrythmic risk, based upon respective time differences between the end of the mechanical and electrical systoles for each of several cardiac cycles for which data is obtained from the subject. For instance, the time difference between the end of the mechanical and electrical systoles can be computed for each cardiac cycle, with the respective time differences used to compute the cardiac-based metric.

In some embodiments, the apparatus 100 includes a denoising module 160 that operates to denoise signals obtained from a subject as acquired by one or both of the acoustical signal acquisition module 140 and the electrical signal acquisition module 150. This denoising module 160 may, for example, be implemented using a denoising approach as discussed herein and/or in the incorporated references/patent documents, such as those discussed in the context of MDSP. Further, this denoising module may be implemented in connection with other modules as shown (separately or together, or with two such denoising modules), such as within the mechanical systole module 110 and within the electrical systole module. In addition, one or more of the modules shown may be implemented in connection with processing circuits and/or a common processing circuit that executes programming to carry out respective functions, such as those involving the identification of systole characteristics, denoising, and the computation of a metric of cardiac risk.

Figure 1B:
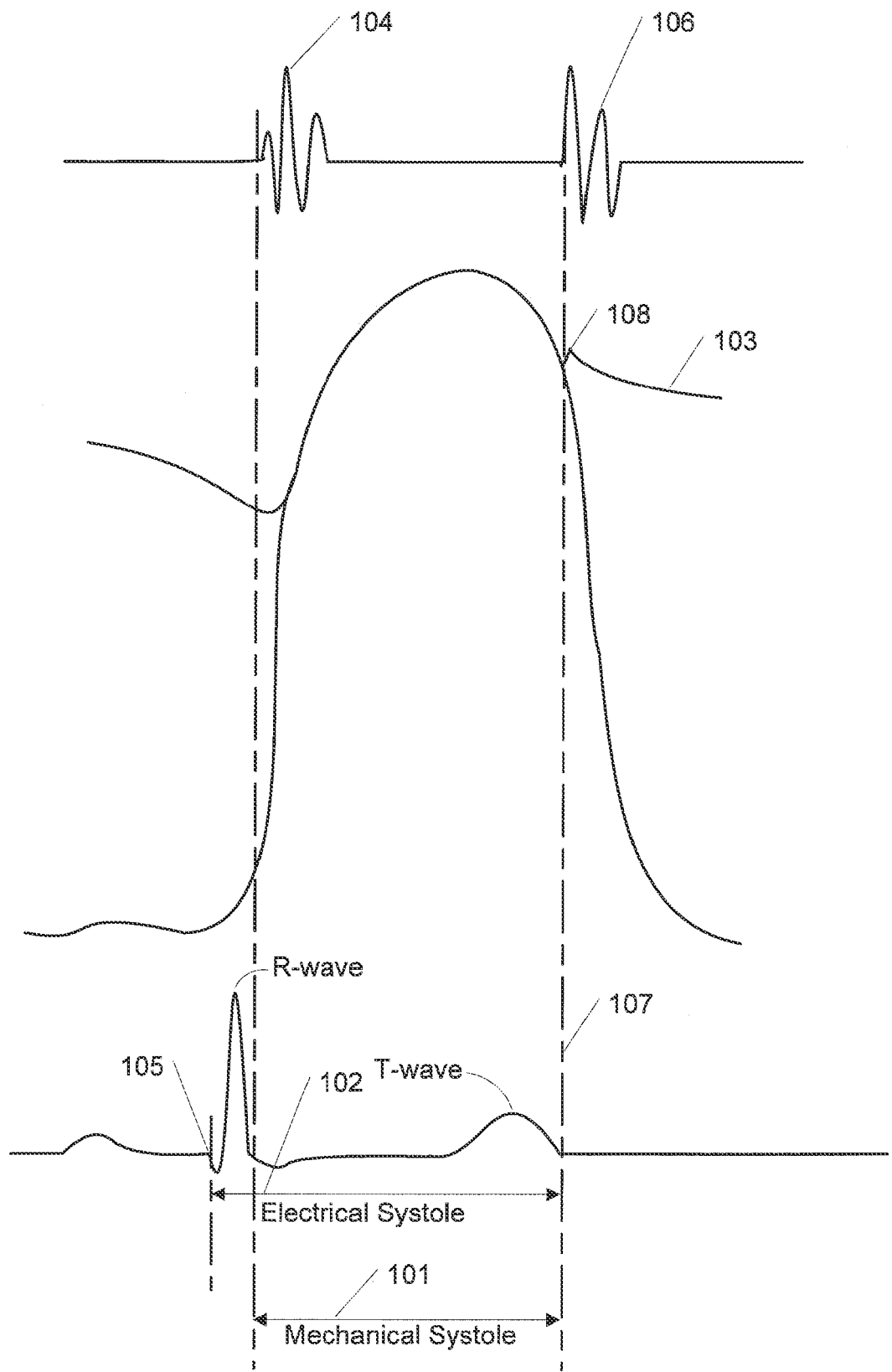
FIG. 1B shows a relationship between heart sounds, arterial blood pressure, left ventricular pressure, and ECG in a subject where EMW duration is <about 20 ms, as processed in connection with the apparatus 100 in FIG. 1A in connection with an example embodiment.

Referring to FIG. 1B, input signals are shown as being processed in accordance with one or more example embodiments, for a normally functioning heart in which the electrical systole 102 begins with the onset of Q-wave 105. The mechanical systole 101 begins immediately prior to an S1 heart sound 104, which occurs concurrent with the opening of the subject's aortic valve. The end of the mechanical and electrical systole at 107 tightly coincide in time, each occurring within about 20 msec of the other, in such a normal heart. An S2 heart sound 106 corresponds to approximately the end of the mechanical systole and the closing of the aortic and pulmonary valves. Inflection point 108 on arterial pressure signal 103 likewise corresponds to approximately the end of the mechanical systole. Inflection point 108 is used to approximate the end of the mechanical systole when arterial pressure is measured immediately adjacent to the heart. At points away from the heart, accommodation is made for delays in the transmission of the pressure wave through the arterial system that result in discordance of the inflection point with the mechanical systole. In some embodiments, the diastolic pressure wave in a peripheral artery is monitored and used to approximate the inflection point of the mechanical systole.

Figure 1C:
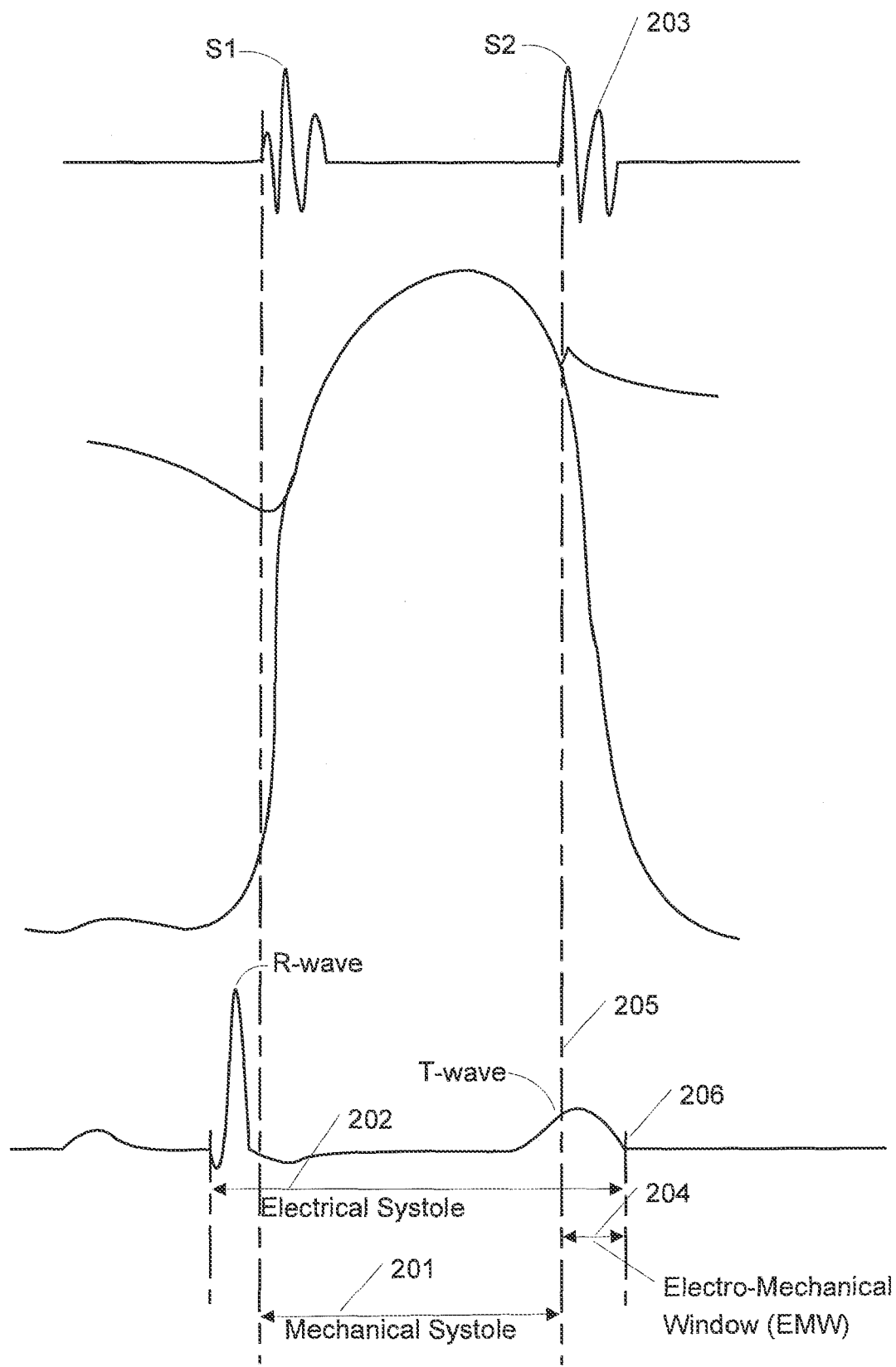
FIG. 1C shows a relationship between heart sounds, arterial blood pressure, left ventricular pressure, and ECG in a subject where EMW duration is longer than about 20 ms, as processed in connection with the apparatus 100 in FIG. 1A in connection with an example embodiment.
Figure 1D:
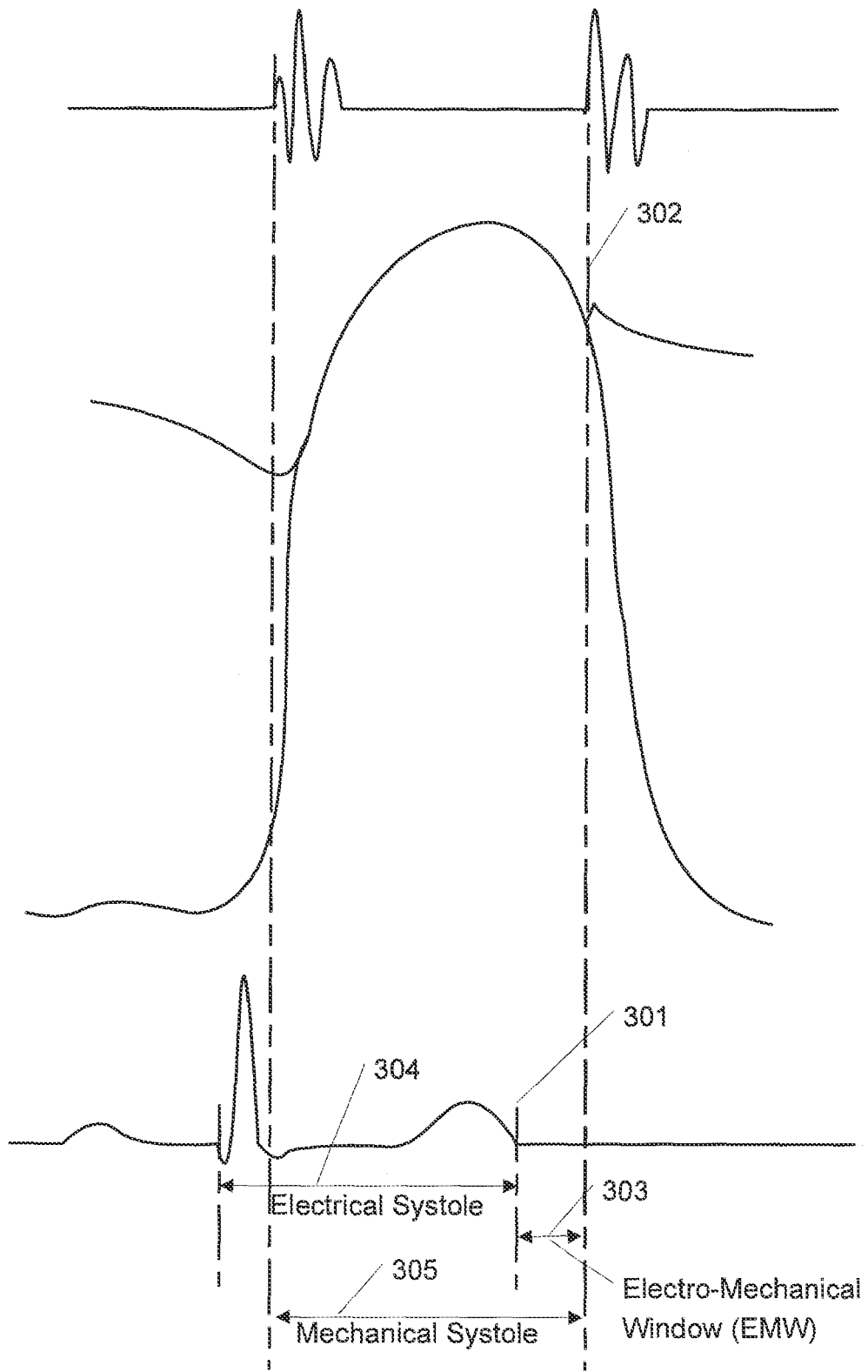
FIG. 1D shows a relationship between heart sounds, arterial blood pressure, left ventricular pressure, and ECG in a subject where EMW duration is negative, as processed in connection with the apparatus 100 in FIG. 1A in connection with an example embodiment.

FIGS. 1C and 1D respectively show signals as used in accordance with various embodiments, to characterize cardiac function in a heart predisposed to cardiac arrhythmias, respectively in which the end of the mechanical systole (MSend) either precedes (as in FIG. 1C) or lags (as in FIG. 1D) the electrical systole (ESend), which may depend upon the nature of the pathophysiology or mechanism of a drug effect. For instance, characteristics can be detected and used to identify a heart that has become predisposed to cardiac arrhythmias due to structural damage in myocardial tissue or by genetic or pro-arrhythmic drug alteration of myocyte ion channels. When this damage occurs, the complex electrophysiological and mechanical interactions that govern heart rhythm may become unbalanced, creating conditions that can lead to arrhythmias. The unbalanced electro-mechanical interactions may occur, at least in part, due to abnormal calcium handling. In the case where the MSend 205 precedes the end of electrical systole 206, as in FIG. 1C, the ventricular muscle is relaxing but is still electrically depolarized and is hence at risk of ventricular arrhythmia. Disassociation of the mechanical and electrical relaxation phases resulting in extension of repolarization into mechanical diastole can trigger Calcium (Ca) sparks in the myocardium, which can lead to Ca waves and Torsades de Pointe. Various embodiments are directed to detecting such characteristics and characterizing related cardiac risk.

Referring to FIG. 1D, the end of mechanical systole 302 lags the electrical systole 301, which are detected via both mechanical and electrical detection and used as an indication that there is a time window in which heart tissue is electrically depolarized but has not yet started to relax. In some embodiments, disassociation of the mechanical and electrical relaxation phases as in this scenario are detected and used to identify conditions established in the myocardium in short QT syndrome (SQTS), such as described in Schimpf, et al., "Electromechanical coupling in patients with the short QT syndrome: Further insights into the mechanoelectrical hypothesis of the U wave," Heart Rhythm, February 2008; 5(2): 241-245, which is fully incorporated herein by reference. Changes in EMW on the order of tens of milliseconds can be highly significant. Accurate and consistent measurements of fiducial points are obtained in both electrical and hemodynamic/mechanical signals, using approaches as described herein.

In various embodiments, measurements of the QT interval (QTI) and the time from the Q onset to the S2 heart sound (QS2) are obtained and used to compute EMW as QS2−QTI. For instance, the Q onset can be detected in addition to the T-offset and S2 heart sound, to arrive at a similar result as in the above discussion.

Long-term (e.g., 24 hours or more) analysis is carried out in accordance with various example embodiments, to assess risk of arrhythmias from subjects ambulatory and/or going about normal activities. This approach involves characterizing the risk of arrhythmias as relative to a time-dependent component, including circadian variation, and is subject to environmental influences such as stress and dosing with a cardioactive drug. This approach can be used, for example, to detect arrhythmia risk markers such as QT prolongation and non-sustained ventricular tachycardia that may not be present during a spot check in the office or clinic. Often these risk markers are unmasked by other contributing factors present in everyday activity such as increased heart rate, stress, or medications. These approaches may be implemented, for example, to address challenges such as those discussed in J. Piccini, et al, "Predictors of sudden cardiac death change with time after myocardial infarction: results from the VALIANT trial," European Heart Journal (2009); and in R. Mayerburg, "Sudden cardiac death: exploring the limits of our knowledge," Journal of Cardiovascular Electrophysiology, Volume 12, No. 3, March (2001), which are fully incorporated herein by reference. Further, various embodiments are directed to accurately identifying T-wave offset in ambulatory subjects using an MDSP approach as described herein, in accordance with one or more embodiments as described in detail in the above-references U.S. Pat. No. 8,433,395, and as described in M. Brockway and R. Hamlin, "Evaluation of an algorithm for highly automated measurements of QT interval," Journal of Pharmacological and Toxicological Methods, vol. 64, pp 16-24 (2011), which is fully incorporated herein by reference.

Various embodiments are directed to addressing challenges to accurately identifying the end of mechanical systole in ambulatory subjects. In one embodiment, EMW measurement is incorporated into an implantable device such as a pacemaker, implantable defibrillator (ICD), implantable cardiac monitor (ICM), or neurostimulation device to add diagnostic and monitoring capability to the device and/or to control therapy delivery based upon EMW measurements. In one embodiment, the device is a pacemaker or ICD with a lead extending into the heart, and the lead contains a pressure sensor to sense a right ventricular pressure. In another embodiment, a pressure sensor is placed in the left ventricle. In one embodiment, the end of mechanical systole is identified as minimum of right or left ventricular pressure (P). In another embodiment, the end of mechanical systole is estimated as a point of a maximum negative right or left ventricular pressure time derivative (max −dP/dt). In another embodiment, the endocardial lead or neurostimulation lead contains a microphone to sense heart sounds. In another embodiment, the lead contains an accelerometer to sense vibrations and movements that coincide with the end of mechanical systole.

Figure 7:
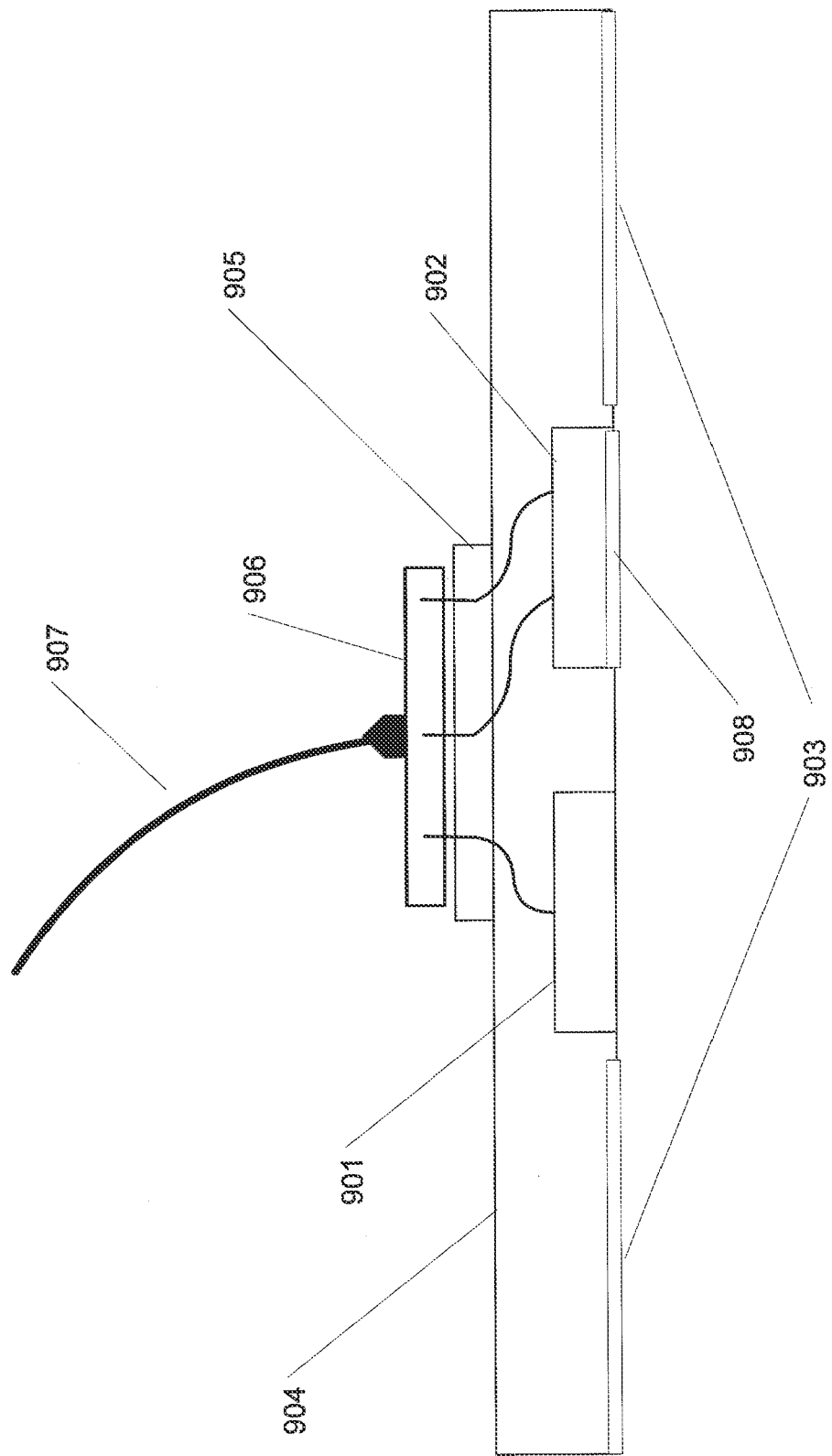
FIG. 7 shows a sensing element for attachment to the skin for sensing S2 heart sounds and ECG from a subject, consistent with an example embodiment.

In another embodiment the end of mechanical systole is identified by a sensor that is sensitive to mechanical vibrations that occur upon closure of the aortic valve (S2 heart sound). In some implementations, such a sensor includes an electronic microphone or an accelerometer placed either under the skin, or in contact with the outer surface of the skin. In some instances in which the sensor is placed under the skin, it is incorporated into an implantable therapeutic or monitoring device. In some implementations involving placement under or on the skin, the sensor includes one or more of a piezoelectric transducer, accelerometer, or microphone. In implementations in which the sensor is placed on the skin, an electronic microphone or accelerometer can be incorporated into an adhesive-backed patch as shown in FIG. 7. In another embodiment, an acoustic sensor is placed in an elastic strap or tight fitting garment that holds the microphone in close contact with the skin.

In one embodiment an accelerometer, microphone, or other sensor capable of converting vibration into an electrical signal is placed subcutaneously or on the skin surface. The signal from the sensor is amplified and filtered to remove noise. In some embodiments an envelope of heart sound signal is computed using low pass-filtering or Hilbert transform. In some embodiments, derivative-based methods are applied to the envelope to generate an emphasis signal. In some embodiments peaks, valleys, and zero crossings of the emphasis signal are evaluated to detect the location of the S2 heart sound.

In some embodiments, a confidence signal is computed and used to assess the validity of a detected S2 location in a manner similar to that described in U.S. patent application Ser. No. 12/938,995, referenced above. If the confidence signal indicates that the detection is invalid or potentially invalid, the system discards the measurement of EMW for that cardiac cycle. In certain embodiments, a confidence signal is computed for a detected T-wave offset in a manner described in U.S. Pat. No. 8,433,395, referenced above. If the confidence signal indicates that the detection is invalid or potentially invalid, the system can discard the EMW measurement for the corresponding cardiac cycle.

In some embodiments, EMW is measured in an implantable cardioverter defibrillator (ICD) and used to predict the onset of ventricular tachycardia (VT) or ventricular fibrillation (VF), and for initiating antitachycardic pacing (antitachy pacing) or overdrive pacing. Predicting the onset of VT or VF seconds or minutes in advance and initiating antitachy or overdrive pacing can be implemented to arrest an arrhythmia without the need for a painful shock delivered by the ICD. In one embodiment, end of electrical systole is detected in the ICD from the endocardial ECG (electrogram) or subcutaneous ECG with electrodes located on or near the ICD. The end of the mechanical systole is detected using one of a number of approaches including an acoustical sensor or accelerometer incorporated into an ICD lead wire, an acoustical sensor incorporated into the ICD can, or a hemodynamic sensor capable of measuring endocardial pressure in communication with the ICD. When using an acoustical sensor or accelerometer, circuitry within the ICD detects the S2 heart sound to indicate MSend. In one embodiment, a hemodynamic sensor measures right ventricular pressure (RVP) and end of mechanical systole is detected as the minimum RVP immediately following the downslope of the RVP waveform in a cardiac cycle or the maximum negative derivative of RVP in a cardiac cycle. In one embodiment, EMW is measured in the ICD or a pacemaker. When the absolute value of EMW consistently exceeds a predetermined threshold, the risk of a life threatening arrhythmia is increased and the ICD delivers antitachy pacing or overdrive pacing is effected for a predetermined period of time to avert the occurrence of a dangerous arrhythmia and the need to deliver a painful defibrillation shock.

In some embodiments, EMW measurements from multiple cardiac cycles are combined to obtain a measure of arrhythmic risk. In other embodiments, measurements of EMW are combined with measurements obtained from other predictors of arrhythmic risk such as QRS duration, QT interval, interval from T-peak to T-offset (TpTo), and T wave alternans (TWA). In one embodiment, a time series of beat-to-beat EMW values is averaged over a predetermined time period (e.g., 30 seconds) to compute a mean EMW value for comparison to a reference normal value as an indicator of risk.

Figure 2:
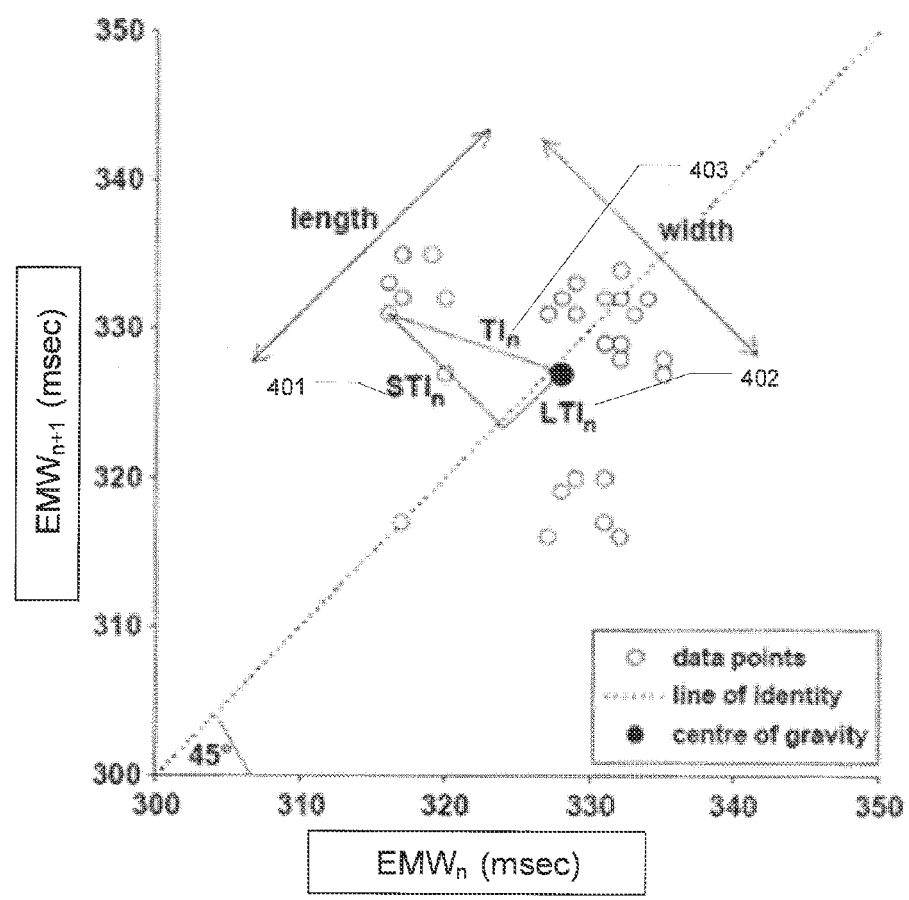
FIG. 2 shows a relationship between EMW dynamics on successive cardiac cycles, consistent with an example embodiment.

The relationships between successive EMW dynamics and the measures on instability based on lag 1 dynamics are implemented to characterize cardiac function as graphically illustrated in FIG. 2 (e.g., as may be implemented with the apparatus 100 as shown in FIG. 1A). In some embodiments, the short term instability (STI) of EMW is computed as an indicator of arrhythmic risk. In one embodiment, STI 401 is computed as the mean of successive differences between beat-to-beat EMW values in a window segment including several (e.g., 10 to 500) cardiac cycles as follows:

$$STI_D = \sum_{i=1}^{N} |D_{n+1} - D_n| / [N\sqrt{2}],$$

where $D_n$ is an EMW measured in the n-th beat and N is the number of beats in the segment.

In another embodiment, short term instability is computed as the standard deviation of successive differences between beat-to-beat EMW values in a segment of N beats. In another embodiment, short term instability is measured as the root mean square of successive differences between beat-to-beat EMW values in a segment of N beats.

In some embodiments, long-term instability (LTI) 402 is computed for a segment of N cardiac cycles in duration as an indicator of arrhythmic risk. LTI is measured as $$LTI_D = \sum_{i=1}^{N} |D_{n+1} + D_n - 2D_{mean}| / [N\sqrt{2}],$$

where $D_n$ is the value of EMW measured for the n-th beat of a segment having a duration of N beats.

In some embodiments a total instability (TI) 403 value is computed by combining STI and LTI, in which TI is computed as the square root of sum of squares of STI and LTI such as $$TI_D = \sqrt{STI_D^2 + LTI_D^2}/\sqrt{2}$$

In some embodiments, the complexity of beat-to-beat interval dynamics is quantified for various risk metrics including QT interval, RR interval, and EMW. In an example embodiment, entropy-based analysis is used to quantify complexity of interval dynamics. For general information regarding entropy-based analysis, and for specific information regarding entropy-based analyses that may be implemented in accordance with one or more example embodiments, reference may be made to the Multiscale Entropy (MSE) approaches as described in M. Costa, A. L. Goldberger, and C.-K. Peng, "Multiscale Entropy Analysis of Complex Physiologic Time Series," Phys. Rev. Lett. 89, 6, (2002), which is fully incorporated herein by reference.

Figure 3A:
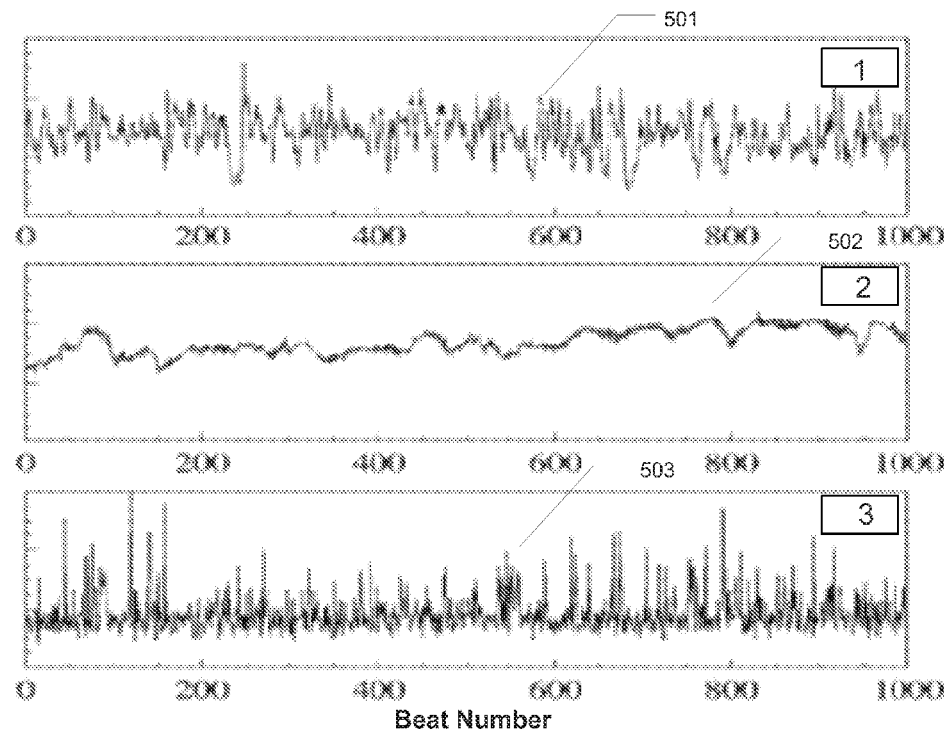
FIG. 3A shows EMW dynamics in a normal heart, consistent with one or more example embodiments.
Figure 3B:
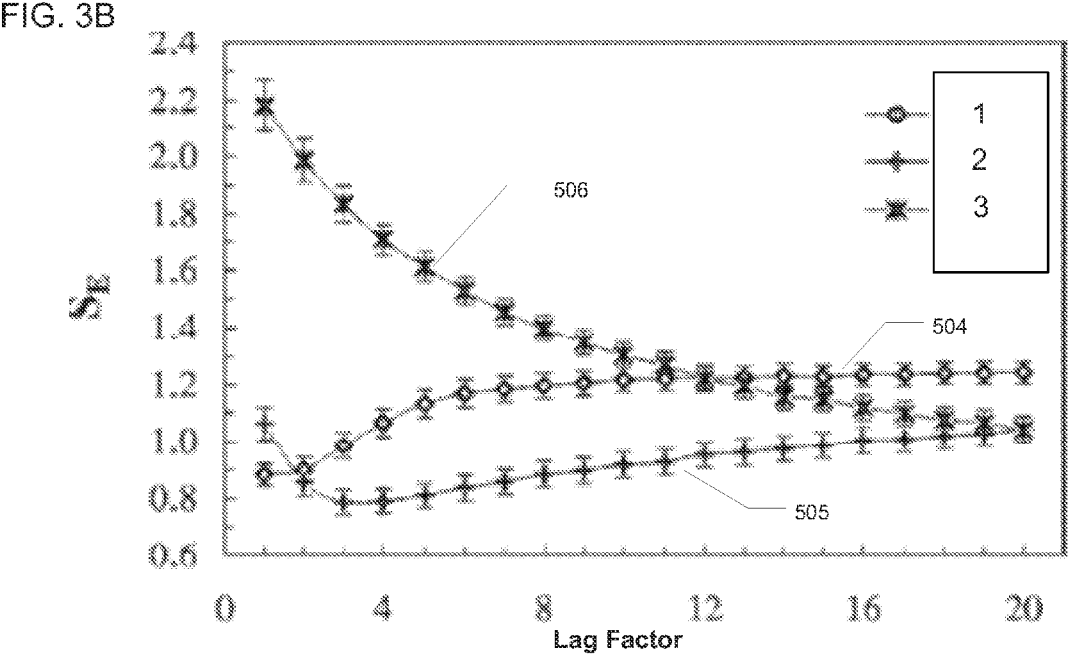
FIG. 3B shows EMW dynamics in a diseased heart, consistent with one or more example embodiments.

Referring to FIGS. 3A and 3B, various example embodiments involving beat-to-beat intervals are shown with respect to plots that are implemented, for example, in computing a cardiac metric (e.g., as may be implemented with the apparatus 100 shown in FIG. 1A). In FIG. 3A, plots 501, 502, and 503 illustrate beat-to-beat R-R interval dynamics with different characteristics: plot 501 shows an example of high variability and high complexity (normal healthy heart); plot 502 shows an example of low variability and low complexity (diseased heart with heart failure); and plot 503 shows and example of high variability and low complexity (diseased heart with atrial fibrillation). Plots 501 and 503 in FIG. 3A are both characterized by high variability. However, plot 501 corresponds to normal dynamics of a healthy heart, and plot 503 illustrates R-R interval dynamics of a diseased heart. These two plots demonstrate that both the healthy and diseased heart can both be characterized by high R-R interval variability, but their physiologic status can be discriminated by assessing complexity of R-R interval dynamics.

Complexity can be quantified using tools, such as multi-scale entropy (MSE), that measure system entropy at various lags. In FIG. 3B, MSE is shown for the corresponding plots 504, 505, and 506, with lags ranging from 1 to 20. In FIG. 3B, plot 504 shows MSE for plot 501 of FIG. 3A, plot 505 shows MSE for plot 502, and plot 506 shows MSE for plot 503. In some embodiments involving these examples, the MSE trend is approximated by a linear equation for the first few lags, and the offset and slope of the linear equation can be used to assess the complexity of interval dynamics. In an example illustrated in plot 506, the low complexity of interval dynamics is characterized by high offset and large negative slope of the linear equation approximating multiscale entropy. High complexity dynamics illustrated in plot 504 are characterized by a relatively lower offset and a positive slope. Referring to FIG. 4A, a diseased heart is identified as exhibiting low complexity interval dynamics as illustrated in plots 601 and 602 in comparison to plots 603 and 604 of FIG. 4B representing normal heart dynamics, such as may be implemented in connection with the apparatus 100 shown in FIG. 1A.

Figure 11:
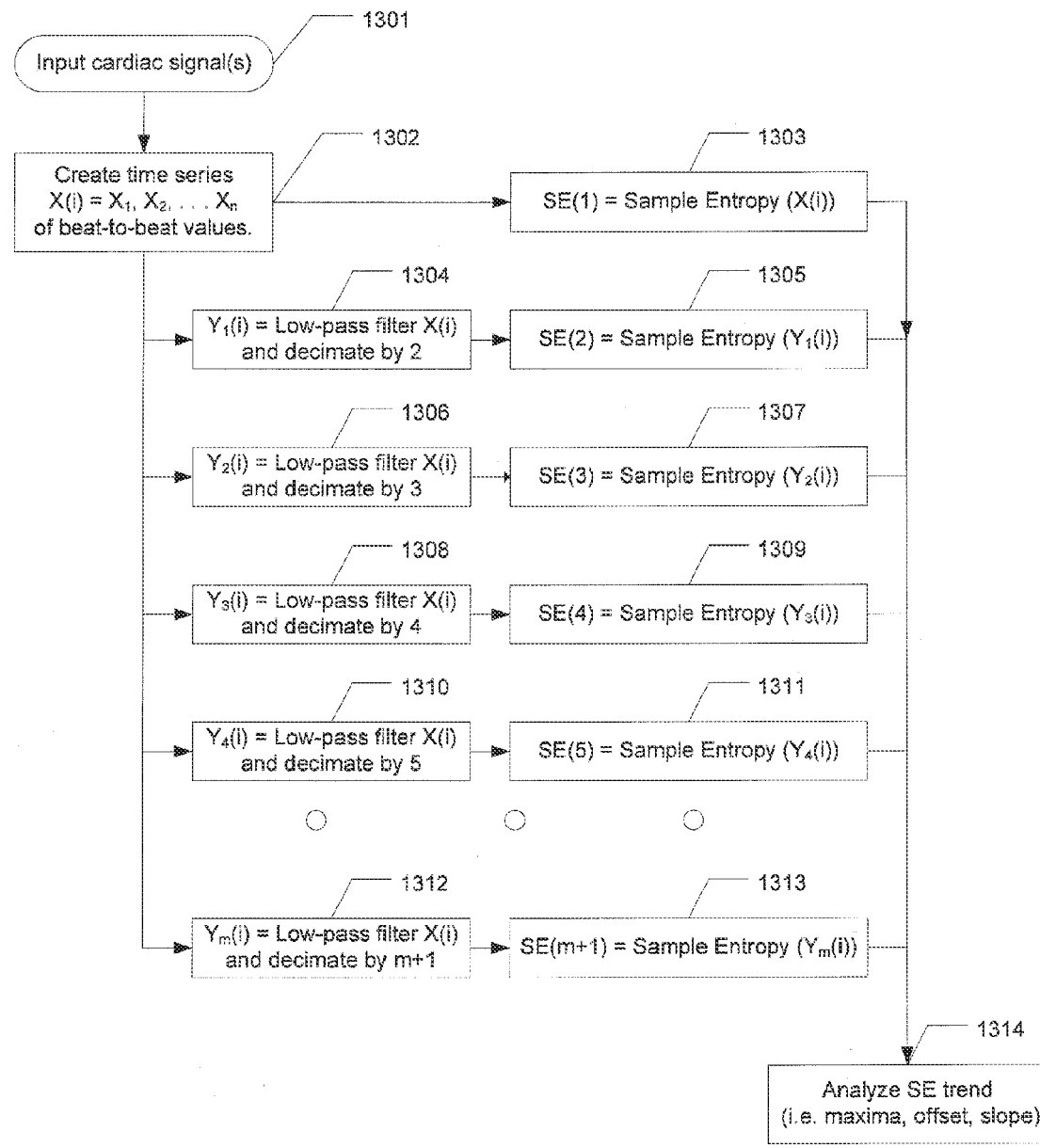
FIG. 11 shows a signal flow diagram for computing and evaluating multiscale entropy of beat-to-beat values detected in a cardiac signal, consistent with another example embodiment.

In an example embodiment, and referring to FIG. 11, multiscale entropy (MSE) is computed and analyzed for assessing risk of arrhythmias or another characteristic of the heart such as atrial fibrillation, coronary ischemia, and an autonomic disturbance due to heart failure. One or more cardiac signals, such as ECG, endocardial pressure, and heart sounds, are input at 1301. A time series X(i) including beat-to-beat values is derived from the cardiac signals in 1302. A time series may include one of QT interval, QS2 interval, R-R interval, T-wave peak amplitude, T-wave area, and EMW=QS2−QT. Time series X(i) may include between 40 and 500 beats, although fewer or more beats may be used.

Time series X(i) is processed to compute sample entropy SE(1) in step 1303. Time series X(i) is further processed to compute sample entropy at multiple lags. For example, in 1304 X(i) is low pass filtered (LPF), decimated to remove every other point, and sample entropy SE(2) is computed for the resulting time series Y1(i) in step 1305. In one embodiment, the frequency cutoff of the LPF is 0.5/(level of decimation). Steps 1306 through 1313 mirror steps 1304 and 1305, and in which the low-pass filter cutoff and the level of decimation are set, for example, with the LPF cutoff in 1304 being ¼ and the level of decimation being 2. The level of decimation corresponds to a lag at which dynamics are evaluated and is also referred to as the scale of the entropy estimate. In 1306, the LPF cutoff is ⅙ and the level of decimation is 3 (2 of every 3 points is removed). In 1308, the LPF cutoff is ⅛ and the level of decimation is 4 (3 of every 4 points is removed). In one embodiment the LPF is an IIR filter such as Butterworth filter. In another embodiment the LPF is an FIR filter such as moving average filter. The number of scales (m+1) as discussed above may be implemented to suit various applications. In one embodiment, the number of scales (m+1) is 10. The resulting trend of sample entropy values, SE(1), SE(2), SE(3), . . . SE(m+1) is analyzed to assess maxima, slope, and offset. In one embodiment, a method used to compute sample entropy is the same for all scales and may be implemented in accordance with the method described in J. S. Richman and J. R. Moorman, "Physiological time-series analysis using approximate entropy and sample entropy," Am. J. Physiol. 278, H2039 (2000), which is fully incorporated by reference.

Figure 10:
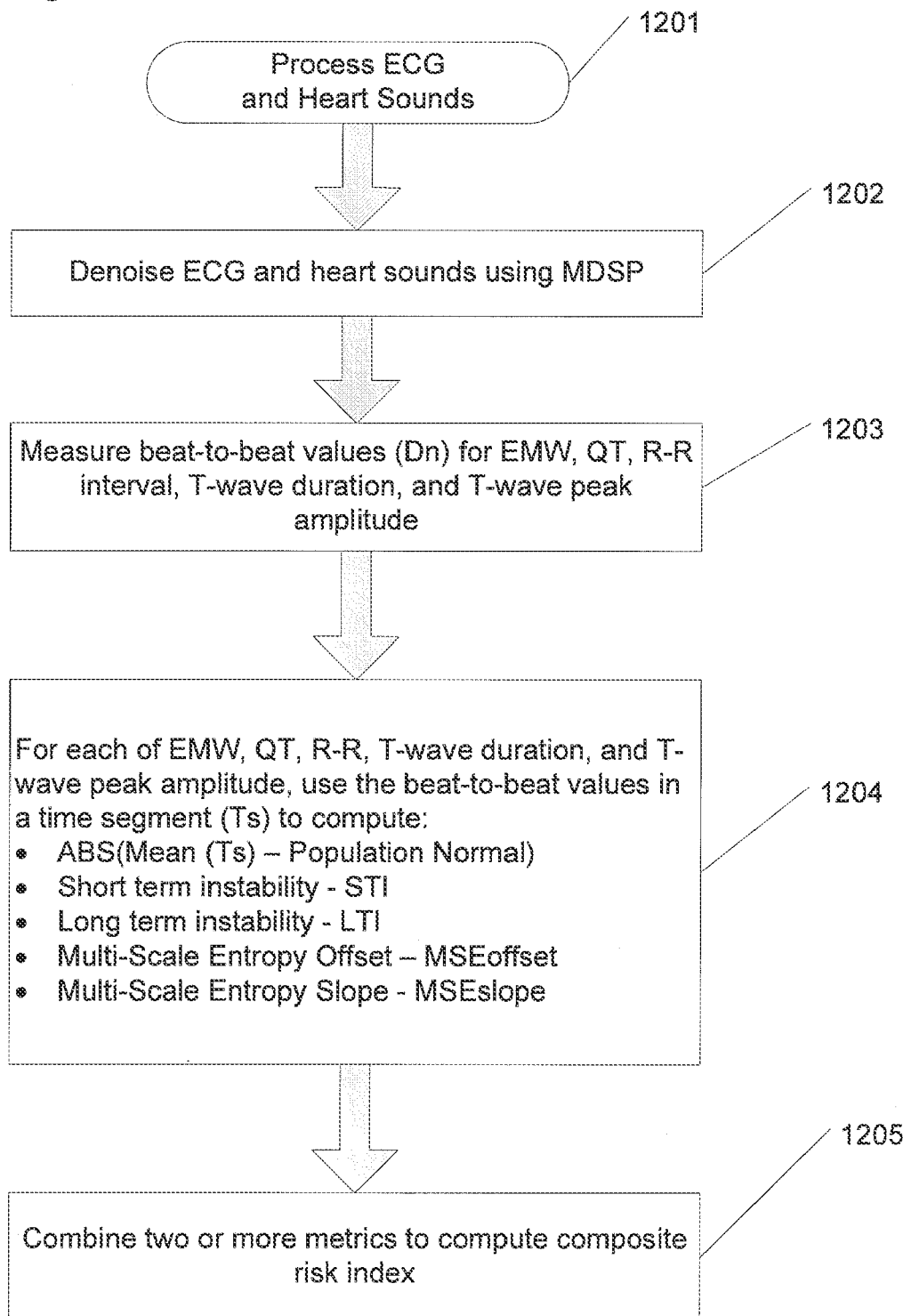
FIG. 10 shows a block diagram for computing a composite metric of arrhythmic risk, consistent with an example embodiment.

Referring to FIG. 10, an example embodiment is shown whereby multiple risk metrics are combined to form a single arrhythmic risk index. In one embodiment, EMW is combined with one or more of a) QRS duration, b) QT interval, c) short term QT instability, and d) TWA. ECG and heart sound signals input at 1201 are processed in 1202 using MDSP and beat-to-beat values of one or more time series Ts of EMW, QT interval, R-R interval, T-wave duration, T-wave area, and T-wave peak amplitude, which are identified in 1203 for a time segment (e.g., 60 seconds). In step 1204, the beat-to-beat values in the time segment are processed to compute a number of risk metrics, such as one or more of: ABS (Mean(Ts)-Normal), Short term instability (STI), Long-term instability (LTI), multi-scale entropy (MSE) offset, and multi-scale entropy (MSE) slope.

In one embodiment, the mean of valid beat-to-beat values (e.g., those obtained from normal cardiac cycles and not corrupted by noise) is computed for the time segment. The population normal value for the metric is subtracted from the mean computed for the segment. The deviation from the normal value is compared to one or more thresholds to assess the level of arrhythmic risk. In another embodiment, STI and LTI are computed and combined to form a total instability metric as described earlier.

In another embodiment, multiscale entropy parameters are used to assess cardiac risk, slope and offset of the linear equation approximating the MSE trend are computed for a QT interval and compared to multiscale entropy parameters of RR interval. Referring to FIG. 4A, an embodiment is shown involving RR interval and QT interval dynamics during heart failure (plots 601 and 602) and normal condition (plots 603 and 604 of FIG. 4B). Referring to 601 and 602 of FIG. 4A, compromised cardiac function is characterized by low variability RR interval dynamics and high variability QT with low complexity. In this case, MSE of QT exhibits high offset and high negative slope while MSE of RR interval exhibits low offset. In contrast, normal cardiovascular function is characterized by high variability RR interval dynamics and low variability QT dynamics as illustrated in plots 603 and 604. In this case, MSE of QT exhibits low offset and normal slope while MSE of RR interval exhibit normal offset and positive slope. An example relationship between the proposed parameters for compromised and normal cardiac function is illustrated in Table 1.

Note that the statistical measures of cardiac intervals shown in Table 1 demonstrate that EMW provides a consistent indicator of cardiac status, whereas QT and RR are often inconsistent.

TABLE 1

Statistical Measures of Cardiac Intervals

|  | Mean | STI | LTI | TI | MSE Offset | MSE Slope |
|---|---|---|---|---|---|---|
| Abnormal Cardiac Function |  |  |  |  |  |  |
| ABS (EMW) | High | High | High | High | High | High, negative |
| QT | High or low | High | High | High | High | High, negative |
| RR | High | Low | Low | Low | Low | Negative |
| Normal Cardiac Function |  |  |  |  |  |  |
| EMW | Low | Low | Low | Low | Normal | Normal |
| QT | Normal | Normal | Normal | Normal | Low | Normal |
| RR | Normal | Normal | Normal | Normal | Normal | Positive |

Figure 5:
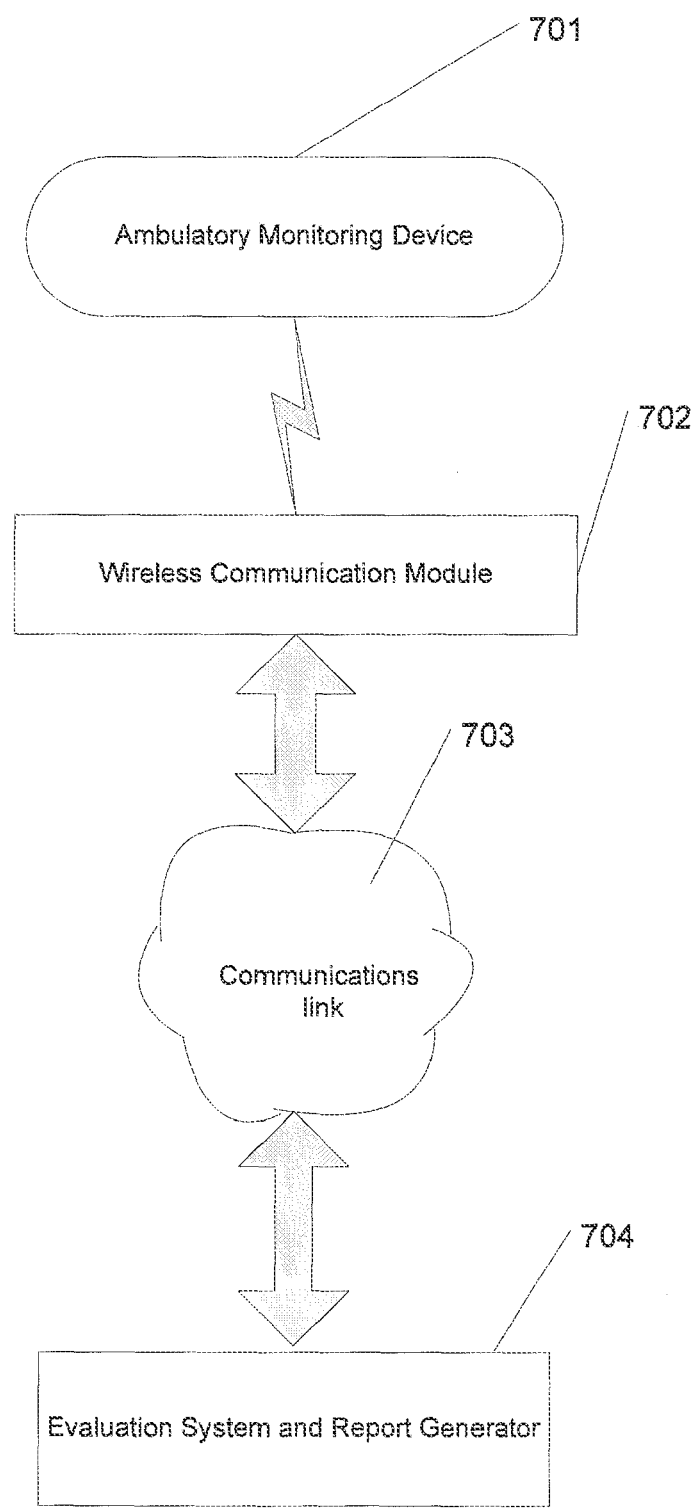
FIG. 5 shows a block diagram of a system for evaluating arrhythmic risk, consistent with an example embodiment.

FIG. 5 shows an embodiment of a system for assessing arrhythmic risk. Ambulatory monitoring device (AMD) 701 receives sensed ECG and heart sounds. A computing device within AMD 701 processes these signals to compute beat-tobeat values for one or more of EMW, QT, R-R, QRS duration. In one embodiment, AMD 701 also evaluates the validity of these computed values using MDSP techniques described in one or more references above (characterized with MDSP). These values are telemetered from AMD 701 to a wireless communication module 702 where they are forwarded via communication link 703 to an evaluation system and report generator (ESRG) 704. The ESRG may, for example, be located in a clinic, laboratory, or service bureau where the received values are reviewed by trained personnel and may be further processed by a computer. In one embodiment, two or more of the received beat-to-beat values are combined in 704 to compute a composite risk index. In some embodiments, AMD 701 detects events of interest, such as arrhythmias, and transmits ECG strips containing those events to wireless communication module 702 and on to ESRG 704. In other embodiments, AMD 701 transmits either segments of the ECG signal (e.g., a 60 second strip) at regular intervals, or a full disclosure ECG and the beat-to-beat values are extracted in ESRG 704.

Figure 6:
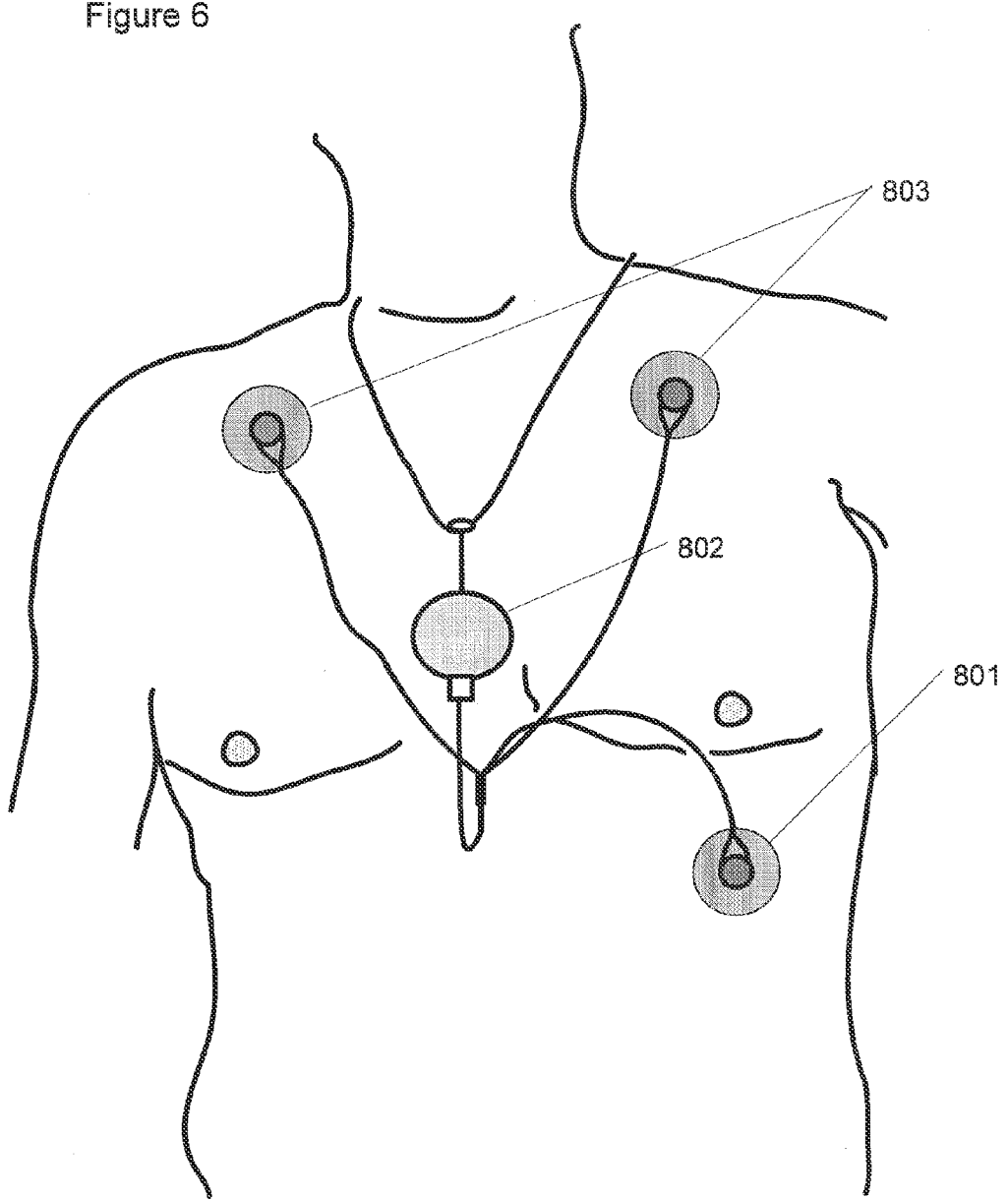
FIG. 6 shows a patient-worn component of a non-invasive system for evaluating arrhythmic risk, consistent with an example embodiment.

FIG. 6 shows an embodiment involving the use of AMD 701 in an implementation in which it is worn by a subject, as implemented with device 802 which includes AMD 701 as well as signal conditioning electronics to process sensed ECG and signals received from acoustical sensors or accelerometers, a computing circuit to denoise the sensed signals and extract beat-to-beat values, a communication circuit to wirelessly telemeter information to wireless communication module 702, and a battery to power the circuits. AMD 701 receives sensed ECG from electrodes 803 and sensed ECG and acoustical or accelerometer signals from combined ECG electrode and acoustical sensor 801. In some embodiments, a combined ECG and acoustical sensor 801 is implemented at each electrode location. This can provide redundancy when sensing the acoustical signal and improve noise immunity by processing signals received from multiple acoustical sensors concurrently to improve the accuracy of S2 heart sound detection. In some embodiments, AMD 701 employs more or less (but not less than two) ECG sensing electrodes.

In one embodiment, referring to FIG. 7, 801 includes adhesive backed form 904 at 2 to 3 mm thick with an ECG sensing electrode 901 and an acoustical sensor 902 mounted in a cavity within the foam. Combined ECG and acoustical sensor 801 provides a single patch that can be adhered to the skin surface for measuring ECG and heart sounds, and used to assess the risk of arrhythmias. Sensor 801 includes foam pad 904 with adhesive applied selectively in region 903. ECG sensing area 901 includes a gel material that couples charge from the skin to a silver-silver chloride material that is electrically connected to device 802 via cable 907. Acoustical sensor 902 includes a microphone, accelerometer, or other sensor capable of converting the mechanical vibrations produced by the heart during closing of the aortic valve into an electrical signal. In some embodiments, sensor 902 is coated with an impedance matching material 908 that matches the impedance of the sensing element in sensor 902 with the acoustical impedance of the skin in order to improve the signal-to-noise ratio of the output of sensor 902. Connecting wires extend from sensing elements 901 and 902 to connector 905. Mating connector 906 connectively couples the signals into cable 907 where they are forwarded to the electronics contained within device 802.

Figure 8:
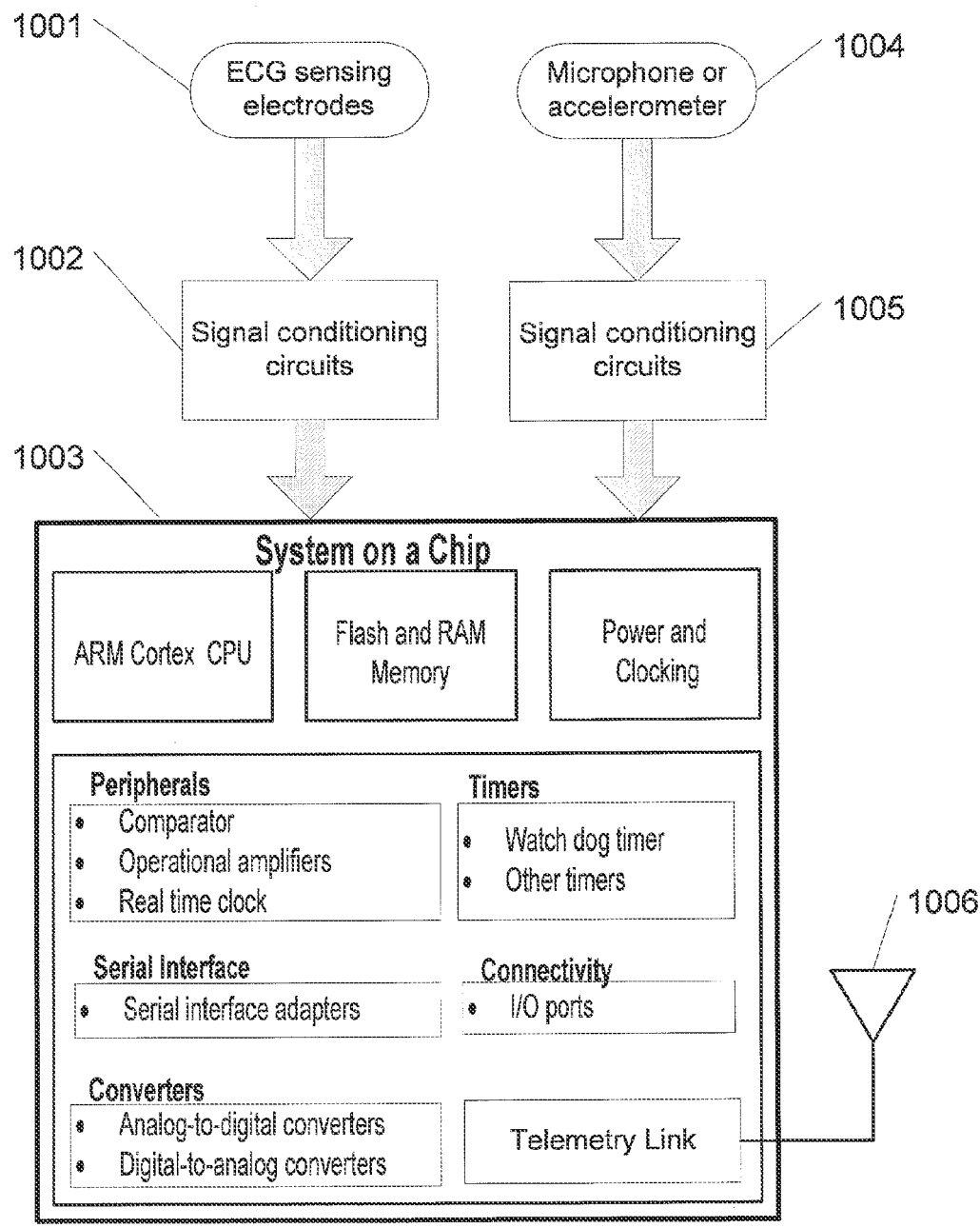
FIG. 8 shows a block diagram of a patient-worn component of a system for evaluating arrhythmic risk, consistent with an example embodiment.

FIG. 8 shows an embodiment involving electronic circuitry that may be contained within AMD 701. Input signals 1001 and 1004 are amplified and filtered to remove noise outside the bandwidth of the signals in signal conditioning circuits 1002 and 1005. In one embodiment, system-on-a-chip 1003 contains analog-to-digital converters to digitize the ECG and acoustical or accelerometer signals, an ARM Cortex microcontroller and associated memory to denoise (e.g. remove in-band noise) and extract beat-to-beat values from the combined ECG and acoustical or accelerometer signals, and a telemetry link and antenna 1006 to wirelessly communicate information to wireless communication module 702.

Figure 9:
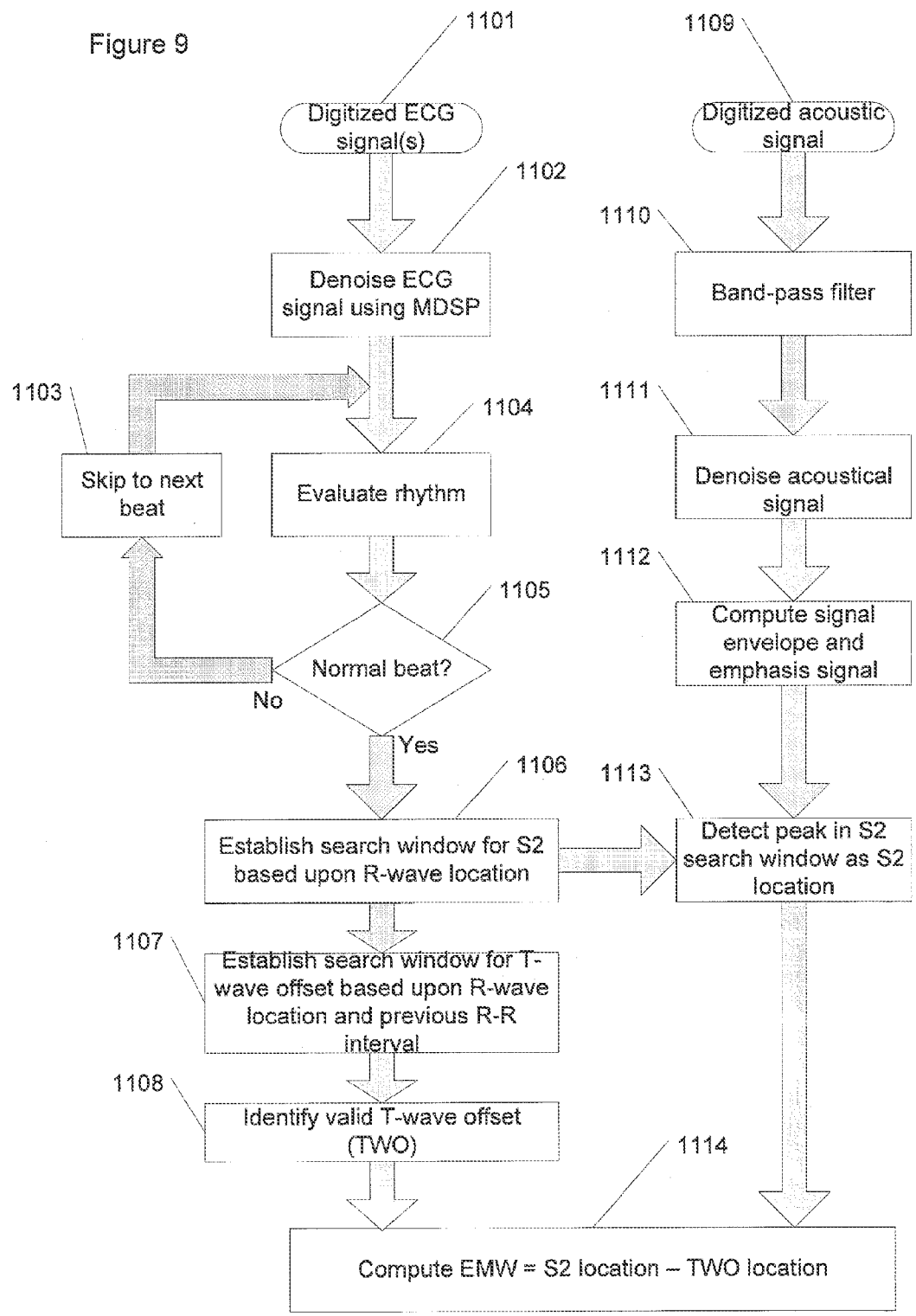
FIG. 9 shows a signal flow diagram for computing electromechanical window, consistent with an example embodiment.

In one embodiment, referring to FIG. 9, EMW is computed using an ECG signal and a digitized acoustical or accelerometer signal. Digitized ECG input signal(s) 1101 are denoised in process 1102 using MDSP to remove in-band noise. The rhythm is evaluated in process 1104 to determine if the current beat is normal or arrhythmic (e.g., premature ventricular contraction, ventricular tachycardia, etc.). If in decision process 1105 it is determined that the beat is arrhythmic, then EMW is not measured and signal flow is directed to the next heart beat via process 1103. If the beat is normal, an S2 search window is established relative to the location of the R-wave in process 1106. For a human being, in some embodiments, the S2 search window begins about 250 msec after the R-wave and extend for about 250 msec. The location of the search window relative to the R-wave is varied based upon species. In some embodiments, the search window location is adjusted on an ongoing basis depending upon the prior RR interval length. In addition, a search window for T-wave offset is also established relative to the R-wave location and the previous R-R interval in process 1107. T-wave offset is identified within the search window and tested for validity using MDSP techniques in process 1108 as described in U.S. patent application Ser. No. 13/172,415, as discussed above.

In one embodiment, digitized input acoustic or accelerometer signal(s) 1109 is (are) band-pass filtered in process 1110 to remove noise outside the pass-band of the S2 heart sounds. In one embodiment band-pass filtering is accomplished using an infinite impulse response filter. In one embodiment, the resulting signal is denoised using signal averaging techniques in process 1111 to remove noise. An envelope of the denoised signal is computed in 1112 using, for example, a Hilbert transform. In some embodiments, derivative-based methods are applied to the envelope to generate an emphasis signal. The resulting emphasis signal is subjected to a peak or threshold detector to identify the S2 heart sound within the search window established in process 1106. EMW is computed in process 1114 as the time difference between the S2 location identified in 1113 and the T-wave offset location identified in 1108. In an alternate embodiment, an emphasis signal is computed based upon process 1407 in FIG. 12 and the peaks, valleys, and zero crossings of the resulting emphasis signal are evaluated to determine the location of the S2 sound.

Figure 12:
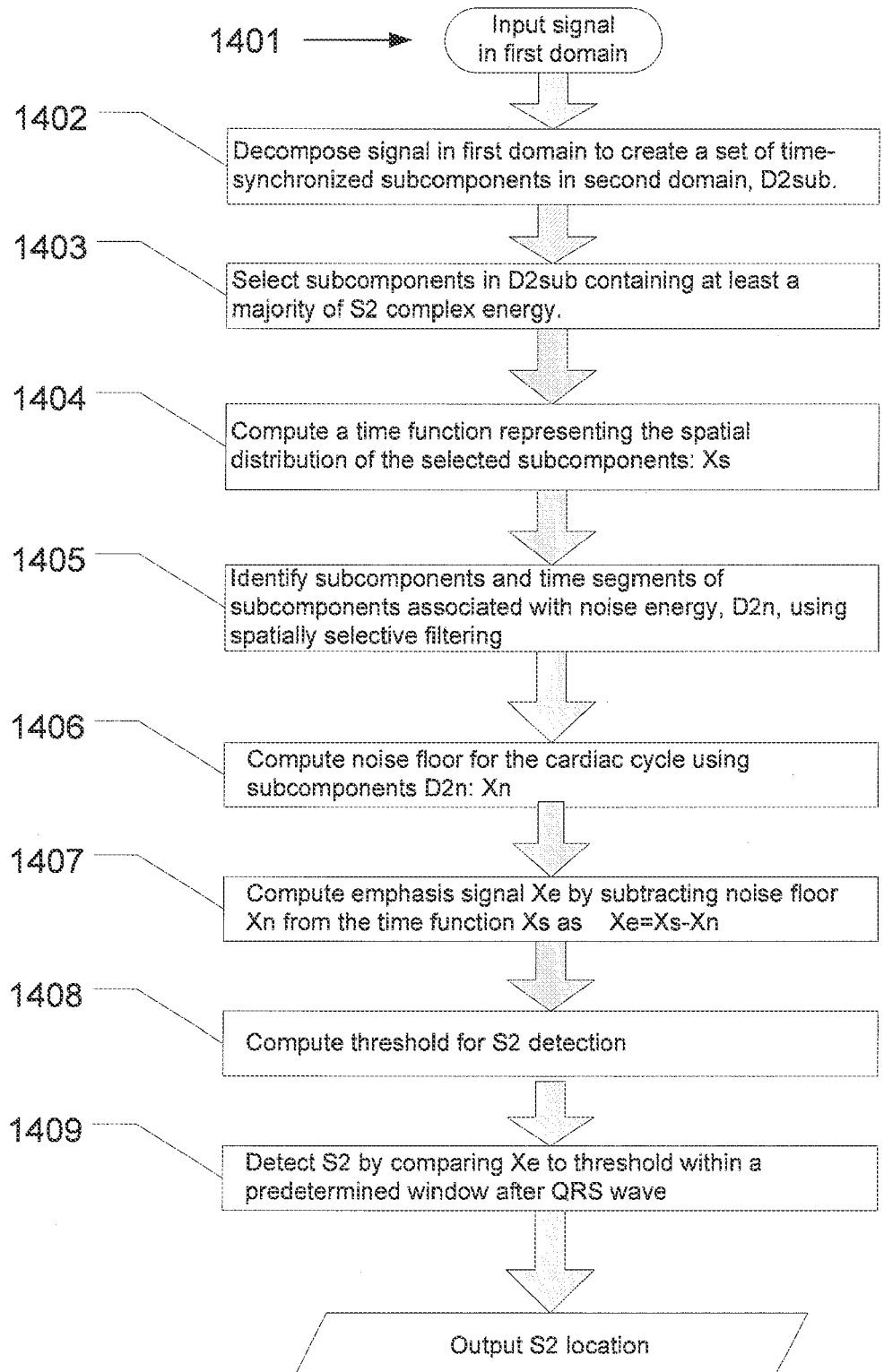
FIG. 12 shows a flow diagram for detecting an S2 heart sound, in accordance with another example embodiment.

In another embodiment, referring to FIG. 12, input signal at 1401 is decomposed to create time synchronized subcomponents in a second domain using one of: a) a discrete cosine transform, b) a wavelet related transform, c) a Karhunen-Loeve transform, d) a short-time Fourier transform, and e) a filter bank. In some embodiments the decomposition is performed in a way that preserves time synchronization of the subcomponents used to compute the time function 1404 in order to achieve an accurate representation of the spatial distribution of the selected subcomponents. To this end, the decomposition uses techniques such as non-orthogonal waveform, undecimated wavelet transform, or stationary wavelet transform.

Subcomponents containing at least a majority of S2 complex energy are selected in 1403. In one embodiment, these subcomponents are selected based upon a priori knowledge of the frequency content of the S2 complexes. Selected subcomponents are combined in 1404 to form a time function Xs that emphasizes the S2 complex. In some embodiments, the time function is formed by computing a point-wise product of the selected subcomponents. In another embodiment, the time function is formed by computing a sum of the selected subcomponents. In yet another embodiment, the time function is formed by computing a cross-correlation function between the selected subcomponents.

Subcomponents and time segments of subcomponents associated with noise energy are identified in step 1405 using spatially selective filtering, such as one or more of the above-referenced patent documents. In step 1406, the noise floor Xn is computed by combining the subcomponents D2$n$ identified in step 1405. In one embodiment, the noise floor is computed on a sample-by-sample basis. In another embodiment, the noise floor is determined by computing the sum of the squares of the subcomponents D2$n$. In another embodiment, an emphasis signal is computed in step 1407 as the difference Xe=Xs−Xn. The threshold of S2 detection is computed in step 1408. In some embodiments the threshold for S2 detection in 1408 is adaptive and changes based on distance from the prior QRS wave. The occurrence of S2 is detected in step 1409 when the time function Xe exceeds the threshold computed in step 1408 within a predetermined window starting from the prior QRS wave.

The various embodiments as discussed herein may be implemented using a variety of structures and related operations/functions. For instance, one or more embodiments as described herein may be computer-implemented or computer-assisted, as by being coded as software within a coding system as memory-based codes or instructions executed by a computer processor, microprocessor, PC or mainframe computer. Such computer-based implementations are implemented using one or more programmable circuits that include at least one computer-processor and internal/external memory and/or registers for data retention and access. One or more embodiments may also be implemented in various other forms of hardware such as a state machine, programmed into a circuit such as a field-programmable gate array, and/or implemented using electronic circuits such as digital or analog circuits. In addition, various embodiments may be implemented using a tangible storage medium that stores instructions that, when executed by a processor, performs one or more of the steps, methods or processes described herein. These applications and embodiments may also be used in combination; for instance certain functions can be implemented using discrete logic (e.g., a digital circuit) that generates an output that is provided as an input to a processor.

Various modules may be implemented to carry out one or more of the operations and activities described herein and/or shown in the figures. In these contexts, a "module" is a circuit that carries out one or more of these related operations/activities (e.g., ascertaining a signal characteristic, or computing a value based upon such ascertained characteristics). For example, in certain of the above-discussed embodiments, one or more modules are discrete logic circuits or programmable logic circuits configured and arranged for implementing these operations/activities, as in the circuit modules shown in the Figures. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the present invention without strictly following the exemplary embodiments and applications illustrated and described herein. For example, different types of signal collecting devices may be used. Such modifications do not depart from the true spirit and scope of the present invention, including that set forth in the following claims.

What is claimed is:

1. A method for computing a cardiac-based metric for use as a predictor of cardiac risk, the method comprising:
for each of a plurality of cardiac cycles of a subject, identifying the end of a mechanical systole based upon an acoustical vibration associated with closure of an aortic valve during the cardiac cycle; and
computing the cardiac-based metric based upon, for each of the plurality of cardiac cycles, a time difference between the end of the mechanical systole and the end of an electrical systole of an electrocardiogram (ECG) signal for the cardiac cycle.

2. The method of claim 1, wherein identifying the end of the mechanical systole includes, in a circuit, processing electronic heart sound data for the cardiac cycle to identify the end of the mechanical systole based on characteristics of the heart sound data.

3. The method of claim 2, further including identifying the end of the electrical systole by, in a circuit, processing electronic ECG signal data for the cardiac cycle to identify the end of the electrical systole based on characteristics of the ECG signal data.

4. The method of claim 1, wherein identifying the end of the mechanical systole includes identifying the end of a mechanical systole using a heart sound signal obtained from the subject during the cardiac cycle.

5. The method of claim 1 further including identifying the end of the electrical systole by identifying a T-wave offset for the ECG signal.

6. The method of claim 1, wherein computing the cardiac-based metric includes computing at least one of:
at least one of a mean and median of the values of the time difference for each cardiac cycle;
at least one of variance, standard deviation, and standard error of the time difference for each cardiac cycle; and
a short-term instability metric by computing one of the mean, standard deviation and root mean square of successive differences between beat-to-beat values in a window segment including the plurality of cardiac cycles.

7. The method of claim 1, wherein computing the cardiac-based metric includes computing
a short-term instability metric by computing one of the mean, standard deviation and root mean square of successive differences between beat-to-beat values in a window segment including the plurality of cardiac cycles, and
a long-term instability metric based on a combination of variance in the beat-to-beat values and the computed short-term instability metric.

8. The method of claim 1, wherein identifying the end of a mechanical systole includes
   detecting the closure of the aortic valve using an acoustical signal containing energy associated with closure of the aortic valve and noise energy,
   decomposing the acoustical signal from a first domain into subcomponents of the acoustical signal in a second domain,
   identifying at least two of the subcomponents that respectively exhibit an energy level of which at least half is associated with closure of the aortic valve, and
   mathematically combining the identified subcomponents to compute a time function that identifiably changes in value upon aortic valve closure.

9. The method of claim 1, wherein the ECG signal includes an ECG component originating from heart tissue of the subject and a noise component, further including identifying the end of the electrical systole by:
   decomposing the ECG signal from a first domain into subcomponents of the ECG signal in a second domain,
   identifying the location of a QRS complex of the cardiac cycle based upon a spatial distribution of the subcomponents,
   identifying a first time window in the cardiac cycle that includes the QRS complex,
   identifying at least one additional time window in the cardiac cycle that does not include the QRS complex,
   for each time window, identify subcomponents having more energy corresponding to the ECG component than noise energy, and
   constructing a denoised ECG in the first domain by combining the identified subcomponents, and using the denoised ECG to identify the end of the electrical systole.

10. The method of claim 1, further including identifying the end of the electrical systole by:
   decomposing the ECG signal from a first domain into subcomponents of the ECG signal in a second domain,
   identifying the location of a QRS complex of the cardiac cycle based upon a spatial distribution of the subcomponents,
   establishing a T-wave offset search window relative to the location of the QRS complex,
   identifying at least two subcomponents having an energy value that is predominantly energy of a T-wave of the cardiac cycle,
   mathematically combining the at least two identified subcomponents to compute an emphasis signal having an identifiable inflection corresponding to a location of the T-wave offset,
   identifying the T-wave offset location based upon a characteristic of the emphasis signal, and
   using the T-wave offset location to identify the end of the electrical systole.

11. An apparatus for computing a cardiac-based metric for use as a predictor of cardiac risk comprising:
   a first module configured and arranged to, for each of a plurality of cardiac cycles of a subject, identify the end of a mechanical systole based upon an acoustical vibration associated with closure of an aortic valve during the cardiac cycle; and
   a second module configured and arranged to compute a cardiac-based metric based upon, for each of the plurality of cardiac cycles, a time difference between the end of the mechanical systole and the end of an electrical systole of an electrocardiogram (ECG) signal for the cardiac cycle.

12. The apparatus of claim 11, further including
   a sensor configured and arranged to convert mechanical vibrations generated by heart sounds of the subject into an electrical heart sound signal, the first module being configured and arranged to receive the heart sound signal and to identify the end of the mechanical systole based upon the acoustical vibration using an acoustical vibration indicated via the received heart sound signal, and
   at least two electrodes configured and arranged to sense the ECG signal from the subject's heart, the second module being configured and arranged to receive the ECG signal.

13. The apparatus of claim 11, further including a third module configured and arranged to identify the end of the electrical systole of the electrocardiogram (ECG) signal for the cardiac cycle.

14. The apparatus of claim 13, wherein the third module is configured and arranged to identify the end of the electrical systole by identifying a T-wave offset for the ECG signal.

15. The apparatus of claim 13, wherein the ECG signal includes an ECG component originating from heart tissue of the subject and a noise component, wherein the third module is configured and arranged to identify the end of the electrical systole by:
   decomposing the ECG signal from a first domain into subcomponents of the ECG signal in a second domain,
   identifying the location of a QRS complex of the cardiac cycle based upon a spatial distribution of the subcomponents,
   identifying a first time window in the cardiac cycle that includes the QRS complex,
   identifying at least one additional time window in the cardiac cycle that does not include the QRS complex,
   for each time window, identify subcomponents having more energy corresponding to the ECG component than noise energy,
   constructing a denoised ECG in the first domain by combining the identified subcomponents, and
   identifying a T-wave offset in the denoised ECG as the end of the electrical systole.

16. The apparatus of claim 13, wherein the third module is configured and arranged to identify the end of the electrical systole by:
   decomposing the ECG signal from a first domain into subcomponents of the ECG signal in a second domain,
   identifying the location of a QRS complex of the cardiac cycle based upon a spatial distribution of the subcomponents,
   establishing a T-wave offset search window relative to the location of the QRS complex,
   identifying at least two subcomponents having an energy value that is predominantly energy of a T-wave of the cardiac cycle,
   mathematically combining the at least two identified subcomponents to compute an emphasis signal having an identifiable inflection corresponding to a location of the T-wave offset,
   identifying the T-wave offset location based upon a characteristic of said emphasis signal, and
   using the T-wave offset location to identify the end of the electrical systole.

17. The apparatus of claim 11, wherein the second module is configured and arranged to compute the cardiac-based metric by computing at least one of:

at least one of a mean, a median, variance, standard deviation, and standard error of the values of the time difference for the cardiac cycles; and a short-term instability metric by computing at least one of the mean, standard deviation and root mean square of successive differences between beat-to-beat values in a window segment including the plurality of cardiac cycles, the beat-to-beat values corresponding to heartbeats that define a successive start of the cardiac cycles.

18. The apparatus of claim 17, wherein the second module is configured and arranged to compute the cardiac-based metric by computing a short-term instability metric based on at least one of the mean, standard deviation and root mean square of successive differences between beat-to-beat values in a window segment including the plurality of cardiac cycles, the beat-to-beat values corresponding to heartbeats that define a successive start of the cardiac cycles, and computing a long-term instability metric by computing a variance in the beat-to-beat values, multiplying the computed variance by two and subtracting the computed short term instability metric.

19. The apparatus of claim 11, wherein the first module is configured and arranged to identify the end of a mechanical systole by detecting the closure of the aortic valve using an acoustical signal containing energy associated with closure of the aortic valve and noise energy, decomposing the acoustical signal from a first domain into subcomponents of the acoustical signal in a second domain, identifying at least two of the subcomponents exhibiting an energy level of which at least half is associated with closure of the aortic valve, and mathematically combining the identified subcomponents to compute a time function that identifiably changes in value upon aortic valve closure.

20. A method comprising:

for each of a plurality of cardiac cycles of a subject, identifying the end of a mechanical systole based upon an acoustical vibration associated with closure of an aortic valve during the cardiac cycle; and computing a cardiac-based metric indicative of arrhythmic risk by:

computing beat-to-beat values of a subject's cardiac function based on, for each of the plurality of cardiac cycles, a time difference between the end of the mechanical systole and the end of an electrical systole of an electrocardiogram (ECG) signal for the cardiac cycle, computing a time series for each of successive lags of the beat-to-beat values by applying a low-pass filter and decimator to the beat-to-beat values, and evaluating the arrhythmic risk based upon a trend of the variability of the time series.

* * * * *